US012751966B2

(12) United States Patent
Kerwin et al.

(10) Patent No.: US 12,751,966 B2
(45) **Date of Patent: *Oct. 6, 2026**

(54) METHODS FOR THE TREATMENT OF CHOLESTEROL CRYSTAL EMBOLIZATION WITH CYCLODEXTRINS

(71) Applicant: Beren Therapeutics P.B.C., West Hollywood, CA (US)

(72) Inventors: Diana Kerwin, West Hollywood, CA (US); Jason Camm, West Hollywood, CA (US)

(73) Assignee: Beren Therapeutics P.B.C., Thousand Oaks, CA (US)

( * ) Notice: Subject to any disclaimer, the term of this patent is extended or adjusted under 35 U.S.C. 154(b) by 248 days.

This patent is subject to a terminal disclaimer.

(21) Appl. No.: 18/043,013

(22) PCT Filed: Aug. 27, 2021

(86) PCT No.: PCT/US2021/048072

§ 371 (c)(1),
(2) Date: Feb. 24, 2023

(87) PCT Pub. No.: WO2022/047241

PCT Pub. Date: Mar. 3, 2022

(65) Prior Publication Data

US 2023/0330133 A1 Oct. 19, 2023

Related U.S. Application Data

(60) Provisional application No. 63/071,222, filed on Aug. 27, 2020.

(51) Int. Cl.

| | |
|---|---|
| ***A61K 31/724*** | (2006.01) |
| ***A61K 9/00*** | (2006.01) |
| ***A61P 3/06*** | (2006.01) |

(52) U.S. Cl.
CPC .......... *A61K 31/724* (2013.01); *A61K 9/0019* (2013.01); *A61P 3/06* (2018.01)

(58) Field of Classification Search
None
See application file for complete search history.

(56) References Cited

U.S. PATENT DOCUMENTS

| | | | | |
|---|---|---|---|---|
| 4,877,778 A | 10/1989 | Carpenter et al. | | |
| 5,403,840 A * | 4/1995 | Vikmon | A61P 9/10 544/138 | |
| 9,675,634 B2 | 6/2017 | Machielse et al. | | |
| 2004/0224011 A1 | 11/2004 | Rodrigueza et al. | | |
| 2008/0293600 A1 | 11/2008 | Goldblatt et al. | | |
| 2014/0005096 A1 | 1/2014 | Schultz et al. | | |
| 2015/0065457 A1 | 3/2015 | Fornoni et al. | | |
| 2016/0361345 A1 | 12/2016 | Machielse et al. | | |
| 2019/0262385 A1 | 8/2019 | Fornoni et al. | | |
| 2022/0008453 A1 | 1/2022 | Hrynkow et al. | | |
| 2023/0302042 A1 | 9/2023 | Kerwin et al. | | |
| 2023/0375576 A1 | 11/2023 | Kerwin et al. | | |
| 2024/0000826 A1 | 1/2024 | Kerwin et al. | | |

FOREIGN PATENT DOCUMENTS

| | | | |
|---|---|---|---|
| WO | 0069412 A1 | 11/2000 | |
| WO | 0154473 A2 | 8/2001 | |
| WO | 2011116245 A2 | 9/2011 | |
| WO | 2013155485 A2 | 10/2013 | |
| WO | 2020086963 A1 | 4/2020 | |
| WO | 2022047241 A1 | 3/2022 | |
| WO | 2022047244 A1 | 3/2022 | |
| WO | 2022047249 A1 | 3/2022 | |
| WO | 2022178318 A1 | 8/2022 | |

OTHER PUBLICATIONS

Ghanem, F., Vodnala, D., Kalavakunta, J. K., Durga, S., Thormeier, N., Subramaniyam, P., . . . & Abela, G. S. (2017). Cholesterol crystal embolization following plaque rupture: a systemic disease with unusual features. Journal of biomedical research, 31(2), 82 (Year: 2017).*
Meyrier, A. (2006). Cholesterol crystal embolism: diagnosis and treatment. Kidney international, 69(8), 1308-1312. (Year: 2006).*
Abi-Mosleh et al. (2009) "Cyclodextrin Overcomes Deficient Lysosome-to-Endoplasmic Reticulum Transport of Cholesterol in Niemann-pick Type C Cells", Proceedings of the National Academy of Sciences of the United States of America, 106(46):19316-21.
Ao et al. (2016) "Effects of Cyclodextrins on the Structure of LDL and Its Susceptibility to Copper-Induced Oxidation", European Journal of Pharmaceutical Sciences, 91:183-189.
Atger et al. (1996) "Cyclodextrins as Catalysts for the Removal of Cholesterol from Macrophage Foam Cells", Department of Biochemistry, Allegheny University of the Health Sciences, 99(4):773-780.
Brewster et al. (Oct. 1989) "An intravenous toxicity study of 2-hydroxypropyf-b-cycle a useful drug solubilizer, in rats and monkeys", International Journal of Pharmaceutics, 59:231-243.
Chen et al. (Nov. 2010) "Cyclodextrin Induces Calcium-Dependent Lysosomal Exocytosis", PLoS One, 5(11): e15054 (7 pages).
Christian et al. (1997) "Use of Cyclodextrins for Manipulating Cellular Cholesterol Content", Department of Biochemistry, Allegheny University of the Health Sciences, Journal of Lipid Research, 38(11): 2264-2272.
Evans et al. (May 2019) "Case Report: Ursodeoxycholic Acid Treatment in Niemann-pick Diease Type C; Clinical Experience in Four Cases", Wellcome Open Research, 2:75 (13 pages).

(Continued)

*Primary Examiner* — Dale R Miller
(74) *Attorney, Agent, or Firm* — Mintz Levin Cohn Ferris Glovsky and Popeo, P.C.

(57) ABSTRACT

Disclosed herein are methods for reducing an amount of and/or a size of, and/or changing the shape of circulating (e.g., blood, serum, plasma) cholesterol crystals (and/or clots comprising cholesterol crystals) in an individual. Further disclosed herein are methods of treating cholesterol crystal embolization (CCE) and/or a symptom thereof in an individual. The methods generally involve administering a therapeutically effective amount of 2-hydroxypropyl-beta-cyclodextrin to the individual. Further provided herein are pharmaceutical compositions comprising a therapeutically effective amount of 2-hydroxypropyl-beta-cyclodextrin and a pharmaceutically acceptable excipient.

12 Claims, 9 Drawing Sheets

(56) References Cited

OTHER PUBLICATIONS

Favier et al. (1995) "Effect of Cyclodextrin on Plasma Lipids and Cholesterol Metabolism in the Rat", Metabolism, 44 (2):200-206.
Fromming et al. (1994) "Pharmacokinetics and Toxicology of Cyclodextrins", Cyclodextrins in Pharmacy, Chapter 3: 33-44.
Gaspar et al. (2017) "2-Hydroxypropyl-Beta-Cyclodextrin (HPBCD) Reduces Age-Related Lipofuscin Accumulation Through a Cholesterol-associated Pathway", Scientific Reports, 7(1):2197 (7 pages).
Gould et al. (Mar. 2005) "2-Hydroxypropyl-b-cyclodextrin (HP-b-CD): A toxicology review", Food and Chemical Toxicology 43 Safety Assessment, AstraZeneca UK Limited, Mereside, Alderley Park, Macclesfield, Cheshire SK10 4TG, United Kingdom, 43(10):1451-1459.
Haynes et al. (2000) "Efflux of Cholesterol From Different Cellular Pools", Biochemistry, 39(15):4508-4517.
Irie et al. (Jun. 1992) "Hydroxypropylcyclodextrins in Parenteral Use. II: Transport and Disposition of Lipids in Rabbit and Effects on Humans", Journal of Pharmaceutical Sciences, 81(6):524-528.
Irie et al. (Feb. 1997) "Pharmaceutical Applications of Cyclodextrins. III. Toxicological Issues and Safety Evaluation", Journal of Pharmaceutical Sciences, 86(2):147-162.
Khera et al. (Jan. 13, 2011) "Cholesterol Efflux Capacity, High-Density Lipoprotein Function, and Atherosclerosis", The New England Journal of Medicine, 364(2):127-135.
Kilsdonk et al. (1995) "Cellular Cholesterol Efflux Mediated by Cyclodextrins", Journal of Biological Chemistry, 270(29):17250-17256.
Kim et al. (2020) "Cyclodextrin Polymer Improves Atherosclerosis Therapy and Reduces Ototoxicity", The Journal of Controlled Release, 319:77-86.
Kritharides et al. (Nov. 1, 1996) "Hydroxypropyl-b-cyclodextrin-mediated Efflux of 7-Ketocholesterol from Macrophage Foam Cells", The Journal of Biological Chemistry, 271(44):27450-27455.
Liu et al. (2003) "Cyclodextrins Differentially Mobilize Free and Esterified Cholesterol From Primary Human Foam Cell Macrophages", Journal of Lipid Research, 44(6):1156-1166.
Lopez et al. (2014) "Systemic Administration of 2-hydroxypropyl-B-cyclodextrin to Symptomatic Npc1-deficient Mice Slows Cholesterol Sequestration in the Major Organs and Improves Liver Function", Clinical and Experimental Pharmacology and Physiology, 41(10):780-787.
Mahjoubin-Tehran et al. (Oct. 2020) "Cyclodextrins: Potential Therapeutics Against Atherosclerosis", Pharmacology & Therapeutics, 214:107620 (42 pages).
Makiela et al. (Jul. 2018) "Investigation of the Influence of B-cyclodextrin on Cholesterol Lodgement—a Molecular Dynamics Simulation Study", Journal of Molecular Liquids, 262:451-459.
Malanga et al. (2016) ""Back to the Future": A New Look at Hydroxypropyl Beta-Cyclodextrins", Journal of Pharmaceutical Sciences, 105(9):2921-2931.
Peake et al. (2012) "Normalization of Cholesterol Homeostasis by 2-hydroxypropyl-b-cyclodextrin in Neurons and Glia Fromm Niemann-pick C1 (Npc1)-deficient Mice", Journal of Biological Chemistry, 287(12):9290-9298.
Pilely et al. (2019) "Alpha-cyclodextrin Inhibits Cholesterol Crystal-induced Complement-Mediated Inflammation: A Potential New Compound for Treatment of Atherosclerosis", Atherosclerosis, 283:35-42.
Pitha et al. (Jun. 1988) "Drug Solubilizers to Aid Pharmacolcgists: Amorphous Cyclooextrin Derivatives", Life Sciences, 43:493-502.
Rosseels et al. (Aug. 2013) "Hydroxypropyl-b-cyclodextrin Impacts Renal and Systemic 4 Hemodynamics in the Anesthetized Dog", Regulatory Toxicology and Pharmacology, 9 pages.
Sakurai et al. (Aug. 2017) "Dietary ?-Cyclodextrin Reduces Atherosclerosis and Modifies Gut Flora in Apolipoprotein E-deficient Mice", Molecular Nutrition & Food Research, 61(8):22 pages.
Singh et al. (Nov. 2019) "High-Density Lipoprotein or Cyclodextrin Extraction of Cholesterol From Aggregated LDL Reduces Foam Cell Formation", The Company of Biologists Ltd., 132(23):jcs. 237271 (6 pages).
Snip et al. (Aug. 2022) "2-Hydroxypropyl-beta-cyclodextrin Treatment Does Not Induce Atherosclerotic Lesion Regression in Western-Type Diet-Fed Apolipoprotein E Knockout Mice", Biomolecules, 12(9):1205 (10 pages).
Song et al. (2014) "2-Hydroxypropyl-B-Cyclodextrin Promotes Transcription Factor Eb-mediated Activation of Autophagy", 289(14):10211-10222.
Stella et al. (2008) "Cyclodextrins", Toxicologic Pathology, 36(1):30-42.
Sun et al. (1994) "Effect of the Platelet-Activating Factor Antagonist BN 50739 and Its Diluents on Mitochondria) Respiration and Membrane Lipids During and Following Cerebral Ischemia", Departments of Neurosurgery and Physiology, University of Wisconsin Medical School, Madison, Wisconsin, U.S.A., 62(5):1929-1938.
Thackaberry et al. (2010) "Comprehensive Investigation of Hydroxypropyl Methylcellulose, Propylene Glycol, Polysorbate 80, and Hydroxypropyl-Beta-Cyclodextrin for use in General Toxicology Studies", Toxicological Sciences, 117(2):485-492.
Uekama, Kaneto (2004) "Design and Evaluation of Cyclodextrin-based Drug Formulation", Chemical and Pharmaceutical Bulletin (Tokyo), 52(8):900-915.
Wang et al. (2019) "Targeting Foam Cell Formation in Atherosclerosis: Therapeutic Potential of Natural Products", Pharmacological Reviews, 71(4):596-670.
Yancey et al. (1996) "Demonstration of Kinetic Pools and Mechanism of Efflux", Journal of Biological Chemistry, 271(27):16026-16034.
Coisne et al. (Dec. 20, 2016) "Cyclodextrins as Emerging Therapeutic Tools in the Treatment of Cholesterol-Associated Vascular and Neurodegenerative Diseases", In Journal of Molecules, 21(12):1748 (22 pages).
Ozkok, Abdullah (2019) "Cholesterol-embolization Syndrome: Current Perspectives", In Journal of Vascular Health and Risk Management, 15:209-220 (13 pages).
Kali, et al. (2024) "Cyclodextrins and Derivatives in Drug Delivery: New Developments, Relevant Clinical Trials, and Advanced Products", Carbohydrate Polymers, 324:121500 (23 pages).
Mendelsohn, et al. (Jun. 2016) "Preclinical Reversal of Atherosclerosis by FDA-Approved Compound that Transforms Cholesterol into an Anti-Inflammatory "Prodrug"", Rejuvenation Research, 19(3):9 pages.
Grebe et al. (Dec. 21, 2016) "Targeting Cholesterol Crystals in Atherosclerosis with Cholesterol Solubilizing 2-hydroxypropyl-b-cyclodextrin", Thesis, Deutsche Nationalbibliothek, 140 pages.
Zimmer et al. (Apr. 6, 2016) "Cyclodextrin Promotes Atherosclerosis Regression via Macrophage Reprogramming", Science Translational Medicine, 8(333):12 pages.
Wang et al. (May 2019) "Cyclodextrin Ameliorates the Progression of Atherosclerosis via Increasing High-Density Lipoprotein Cholesterol Plasma Levels and Anti-inflammatory Effects in Rabbits", Journal of Cardiovascular Pharmacology, 73(5):334-342.
Martinic, Goran (2001) "Cyclodextrins As Potential Human Anti-atherosclerotic Agents", Thesis, Western Sydney University Thesis Collection, 324 pages.
Bakke et al. (Aug. 30, 2017) "Cyclodextrin Reduces Cholesterol Crystal-Induced Inflammation by Modulating Complement Activation", Journal of Immunology, 199(8):2910-2920.
Crumling et al. (Nov. 2017) "Cyclodextrins and Iatrogenic Hearing Loss: New Drugs with Significant Risk", Frontiers in Cellular Neuroscience, 11(355):14 pages.
Walenbergh, S.M.A., et al., "Weekly Treatment of 2-Hydroxypropyl-b-cyclodextrin Improves Intracellular Cholesterol Levels in LDL Receptor Knockout Mice", International Journal of Molecular Sciences (2015) vol. 16, pp. 21056-21069 Abstract; Discussion at p. 21063; Experimental at pp. 21064-21065; Figs. 2-3.
Mitrofanova, A., et al., "Hydroxypropyl-b-cyclodextrin protects from kidney disease in experimental Alport syndrome and focal segmental glomerulosclerosis", Kidney International (2018) vol. 94, pp. 1151-1159 Abstract; Sections: Results at pp. 1152-1153, Discussion at p. 1156; Figs. 1-4, 6.
(Jul. 6, 2005) "Guidance for Industry Estimating the Maximum Safe Starting Dose in Initial Clinical Trials for Therapeutics in Adult Healthy Volunteers", U.S. Department of Health and Human Ser-

(56) References Cited

OTHER PUBLICATIONS vices Food and Drug Administration Center for Drug Evaluation and Research (CDER), Pharmacology and Toxicology, 30 pages.
U.S. Appl. No. 17/242,104, filed Apr. 27, 2021, 48 pages.
Kannel, William B. (1998) "Overview of Atherosclerosis", Clinical Therapeutics, 20(Supplement B):B2-B17 (16 Pages).
Raal et al. (Sep. 28, 2018) "Familial Hypercholesterolemia Treatments: Guidelines and New Therapies", Atherosclerosis, 277:483-492.
Zimmer, et al. (2016) "Cyclodextrin Promotes Atherosclerosis Regression via Macrophage Reprogramming", Supplementary Materials, Science Translational Medicine, 8(333):35 pages.
Reagan-Shaw et al. (2007) "Dose Translation from Animal to Human Studies Revisited", The Federation of American Societies for Experimental Biology Journal, 22(3):659-661.

* cited by examiner

METHODS FOR THE TREATMENT OF CHOLESTEROL CRYSTAL EMBOLIZATION WITH CYCLODEXTRINS

CROSS-REFERENCE TO RELATED APPLICATIONS

This application is a National Stage Application filed under 35 U.S.C. § 371 of International Patent Application No. PCT/US2021/048072, filed Aug. 27, 2021, which claims the benefit of priority to U.S. Provisional Patent Application Ser. No. 63/071,222, filed Aug. 27, 2020, the contents of are hereby incorporated by reference in their entireties.

BACKGROUND

Cholesterol crystal embolization (CCE) (also termed “atheroembolism”, “atheromatous embolization syndrome”, or “cholesterol embolization syndrome”) is a systemic disease thought to be caused by the showering of cholesterol crystals from large blood vessels (e.g., the aorta), often due to the rupture of atherosclerotic plaques, to the distal circulation and causing an obstruction of smaller arteries and other blood vessels. CCE has various clinical manifestations, including renal, cutaneous, central nervous system, intestinal, and ocular manifestations, among others. CCE is thought to be most commonly iatrogenic, such as a complication of medical procedures involving the blood vessels; however, CCE can also occur spontaneously in some patients (e.g., those with advanced atherosclerosis). There is no known therapy that has been shown to alter the course of CCE. Preclinical data suggest 2-hydroxypropyl-beta-cyclodextrins could have profound beneficial effects on the pathomechanisms responsible for CCE by reducing the amount of and/or size of, and/or changing the shape of circulating cholesterol crystals (and/or clots comprising cholesterol crystals). Therefore, 2-hydroxypropyl-beta-cyclodextrins may provide a novel treatment option for CCE and symptoms thereof.

SUMMARY OF THE DISCLOSURE

There is a need for effective treatments of cholesterol crystal embolization (CCE) and/or symptoms thereof. This disclosure addresses this unmet need.

In one aspect, a method is provided for reducing an amount of, reducing a size of, and/or changing the shape of circulating cholesterol crystals and/or clots comprising cholesterol crystals in an individual, the method comprising: administering a therapeutically effective amount of 2-hydroxypropyl-beta-cyclodextrin to the individual, thereby reducing the amount of, reducing the size of, and/or changing the shape of circulating cholesterol crystals in the individual. In some cases, the size of circulating cholesterol crystals and/or clots comprising cholesterol crystals is reduced by at least about 10%, at least about 15%, at least about 20%, at least about 25%, at least about 30%, at least about 35%, at least about 40%, at least about 45%, at least about 50%, or greater than 50%, relative to the size of circulating cholesterol crystals and/or clots comprising cholesterol crystals prior to the administering with the 2-hydroxypropyl-beta-cyclodextrin. In some cases, the size of the circulating cholesterol crystals and/or clots comprising cholesterol crystals is an average size or a maximum size. In some cases, the amount of circulating cholesterol crystals and/or clots comprising cholesterol crystals is reduced by at least about 10%, at least about 15%, at least about 20%, at least about 25%, at least about 30%, at least about 35%, at least about 40%, at least about 45%, at least about 50%, or greater than 50%, relative to the amount of circulating cholesterol crystals and/or clots comprising cholesterol crystals prior to the administering with the 2-hydroxypropyl-beta-cyclodextrin. In some cases, the amount of circulating cholesterol crystals is a concentration of circulating cholesterol crystals. In some cases, the circulating cholesterol crystals are found in blood, plasma, or serum. In some cases, the treating reduces an incidence or severity of cholesterol crystal embolization (CCE) in the individual.

In another aspect, a method is provided for treating cholesterol crystal embolization (CCE) and/or one or more symptoms thereof in an individual, the method comprising: administering a therapeutically effective amount of 2-hydroxypropyl-beta-cyclodextrin to the individual, thereby treating the CCE and/or one or more symptoms thereof in the individual. In some cases, the treating comprises reducing a size of circulating cholesterol crystals and/or clots comprising cholesterol crystals in the individual. In some cases, the size of circulating cholesterol crystals and/or clots comprising cholesterol crystals is a maximum size or an average size. In some cases, the treating comprises reducing an amount of circulating cholesterol crystals and/or clots comprising cholesterol crystals in the individual. In some cases, the amount of circulating cholesterol crystals and/or clots comprising cholesterol crystals is a concentration of circulating cholesterol crystals. In some cases, the treating comprises changing a shape of circulating cholesterol crystals and/or clots comprising cholesterol crystals in the individual. In some cases, the treating comprises reducing inflammation in the individual. In some cases, the inflammation is measured by cytokine protein and/or RNA levels. In some cases, the treating comprises improving renal function in the individual. In some cases, the treating comprises improving dermatologic manifestations in the individual. In some cases, the treating comprises improving eosinophilia in the individual. In some cases, the treating comprises improving hematologic abnormalities in the individual. In some cases, the treating comprises improving complement levels in the individual. In some cases, the treating comprises improving proteinuria in the individual.

In some cases, the therapeutically effective amount is from about 50 mg/kg to about 2,500 mg/kg. In some cases, the therapeutically effective amount is from about 4 g to about 250 g. In some cases, the therapeutically effective amount is an amount sufficient to achieve a serum, plasma, and/or whole blood concentration of 2-hydroxypropyl-beta-cyclodextrin of about 0.01 mM to about 3 mM. In some cases, the therapeutically effective amount is an amount effective to increase a circulating and/or systemic level of one or more oxysterol in the individual by at least about 10% after the administering as compared to prior to the administering. In some cases, the one or more oxysterol is 24S-hydroxycholesterol, 27-hydroxycholesterol, or both. In some cases, the therapeutically effective amount is an amount effective to plasma cholesterol crystal dissolution capacity (CCDC) by at least about 10% after the administering as compared to prior to the administering. In some cases, the therapeutically effective amount is an amount effective to increase mRNA levels of ABCA1 and/or ABCG1 by at least about 10% after the administering as compared to prior to the administering. In some cases, the 2-hydroxypropyl-beta-cyclodextrin is selected from the group consisting of: Kleptose® HP Parenteral Grade, Kleptose® HPB Parenteral Grade, Kleptose® HPB-LB Parenteral Grade, Cavitron® W7 HP5 Pharma cyclodextrin, Cavitron® W7 HP7 Pharma cyclodextrin, Trappsol® Cyclo™, and VTS-270/adrabetadex. In some cases, the individual has one or more risk factors for CCE. In some cases, the one or more risk factors for CCE is selected from the group consisting of: interventional vascular procedures, interventional diagnostic procedures, cardiovascular surgery, cardiovascular disease (e.g., coronary artery disease, atherosclerotic cardiovascular disease), aortic aneurysm, aortic plaque, hypertension, diabetes mellitus, hyperlipidemia, smoking, being of the male sex, age, increased inflammation (e.g., increased serum (hs)CRP levels), anticoagulation, thrombolytic treatment, and any combination thereof. In some cases, the individual has one or more analytical lab results associated with CCE. In some cases, the one or more analytical lab results associated with CCE is selected from the group consisting of: increased serum creatinine, leukocytosis, eosinophilia, anemia, thrombocytopenia, hypocomplementemia, increased erythrocyte sedimentation rate, increased (hs)CRP levels, increased fibrinogen levels, eosinophiluria, proteinuria, hematuria, abnormal liver enzymes, and any combination thereof. In some cases, the individual is at least 30 years old. In some cases, the individual is a human. In some cases, the administering further comprises: (i) administering, at a first time point, a therapeutically effective first dose of 2-hydroxypropyl-beta-cyclodextrin to the individual; and (ii) administering, at a second time point, a therapeutically effective second dose of 2-hydroxypropyl-beta-cyclodextrin to the individual. In some cases, the second time point is at least 4 hours, at least 6 hours, at least 8 hours, at least 12 hours, at least 1 day, at least 2 days, at least 3 days, at least 4 days, at least 5 days, at least 6 days, at least 1 week, at least 2 weeks, at least 3 weeks, or at least 4 weeks after the first time point. In some cases, the administering is by intravenous administration.

In another aspect, a pharmaceutical composition is provided comprising: an amount of 2-hydroxypropyl-beta-cyclodextrin effective to reduce an amount of, reduce a size of, and/or change a shape of circulating cholesterol crystals and/or clots comprising cholesterol crystals in an individual; and a pharmaceutically acceptable excipient. In yet another aspect, a pharmaceutical composition is provided comprising: an amount of 2-hydroxypropyl-beta-cyclodextrin effective to treat cholesterol crystal embolization (CCE) and/or a symptom thereof, in an individual; and a pharmaceutically acceptable excipient. In some cases, the amount of 2-hydroxypropyl-beta-cyclodextrin is an amount effective to increase a circulating and/or systemic level of one or more oxysterols in the individual by at least about 10% after administering the pharmaceutical composition to the individual. In some cases, the one or more oxysterols is 24S-hydroxycholesterol, 27-hydroxycholesterol, or both. In some cases, the amount of 2-hydroxypropyl-beta-cyclodextrin is an amount effective to increase plasma cholesterol crystal dissolution capacity (CCDC) in the individual by at least about 10% after administering the pharmaceutical composition to the individual. In some cases, the amount of 2-hydroxypropyl-beta-cyclodextrin is an amount effective to increase mRNA levels of ABCA1 and/or ABCG1 in the individual by at least about 10% after administering the pharmaceutical composition to the individual. In some cases, the pharmaceutical composition is formulated for single dose administration. In some cases, the pharmaceutical composition is formulated for intravenous administration.

In yet another aspect, a kit is provided comprising: (a) one or more container; and (b) the pharmaceutical composition of any one of the preceding, wherein the pharmaceutical composition is contained within the one or more container. In some cases, the kit further comprises (c) instructions for use of the pharmaceutical composition for reducing an amount of, reducing a size of, and/or changing the shape of circulating cholesterol crystals and/or clots comprising cholesterol crystals in an individual, and/or for treating cholesterol crystal embolization (CE) and/or one or more symptoms thereof in an individual. In some cases, at least one of the one or more container is an IV infusion bag. In some cases, the one or more container comprises a single container comprising the pharmaceutical composition and one or more additional active pharmaceutical ingredients. In some cases, the one or more container comprises a first container containing the pharmaceutical composition and a second container containing one or more additional active pharmaceutical ingredients. In some cases, the kit further comprises one or more additional components selected from the group consisting of: an IV infusion bag, a catheter, tubing, a needle, a syringe, a solution, and any combination thereof.

In another aspect, a method of reducing an amount of and/or a size of, and/or changing a shape of circulating (e.g., blood, serum, plasma) cholesterol crystals (and/or clots comprising cholesterol crystals) in an individual is provided, the method comprising: administering a therapeutically effective amount of 2-hydroxypropyl-beta-cyclodextrin to the individual, thereby reducing the amount of and/or size of, and/or changing the shape of circulating cholesterol crystals (and/or clots comprising cholesterol crystals) in the individual. In some cases, the size (e.g., average size, maximum size) of circulating (e.g., blood, serum, plasma) cholesterol crystals (and/or clots comprising cholesterol crystals) is reduced by at least about 10% (e.g., at least about 15%, at least about 20%, at least about 25%, at least about 30%, at least about 35%, at least about 40%, at least about 45%, at least about 50%, or greater) relative to the size (e.g., average size, maximum size) of circulating (e.g., blood, serum, plasma) cholesterol crystals (and/or clots comprising cholesterol crystals) prior to treatment with the 2-hydroxypropyl-beta-cyclodextrin. In some cases, the amount (e.g., concentration) of circulating (e.g., blood, serum, plasma) cholesterol crystals (and/or clots comprising cholesterol crystals) is reduced by at least about 10% (e.g., at least about 15%, at least about 20%, at least about 25%, at least about 30%, at least about 35%, at least about 40%, at least about 45%, at least about 50%, or greater) relative to the amount (e.g., concentration) of circulating (e.g., blood, serum, plasma) cholesterol crystals (and/or clots comprising cholesterol crystals) prior to treatment with the 2-hydroxypropyl-beta-cyclodextrin. In some cases, the treating reduces an incidence of or severity of cholesterol crystal embolization (CCE) in the individual.

In another aspect, a method of treating cholesterol crystal embolization (CCE) and/or one or more symptoms thereof in an individual is provided, the method comprising: administering a therapeutically effective amount of 2-hydroxypropyl-beta-cyclodextrin to the individual, thereby treating the CCE and/or one or more symptoms thereof in the individual. In some cases, the treating comprises reducing a size and/or an amount of circulating (e.g., blood, plasma, serum) cholesterol crystals (and/or clots comprising cholesterol crystals) in the subject. In some cases, the size (e.g., average size, maximum size) of circulating (e.g., blood, serum, plasma) cholesterol crystals (and/or clots comprising cholesterol crystals) is reduced by at least about 10% (e.g., at least about 15%, at least about 20%, at least about 25%, at least about 30%, at least about 35%, at least about 40%, at least about 45%, at least about 50%, or greater) relative to the size (e.g., average size, maximum size) of circulating (e.g., blood, serum, plasma) cholesterol crystals (and/or clots comprising cholesterol crystals) prior to treatment with the 2-hydroxypropyl-beta-cyclodextrin. In some cases, the amount (e.g., concentration) of circulating (e.g., blood, serum, plasma) cholesterol crystals (and/or clots comprising cholesterol crystals) is reduced by at least about 10% (e.g., at least about 15%, at least about 20%, at least about 25%, at least about 30%, at least about 35%, at least about 40%, at least about 45%, at least about 50%, or greater) relative to the amount (e.g., concentration) of circulating (e.g., blood, serum, plasma) cholesterol crystals (and/or clots comprising cholesterol crystals) prior to treatment with the 2-hydroxypropyl-beta-cyclodextrin. In some cases, the treating results in a change in shape of circulating cholesterol crystals (and/or clots comprising cholesterol crystals). In some cases, the treating results in a decrease in inflammation (e.g., as measured by, e.g., cytokine protein and/or RNA levels) as compared to a level of inflammation prior to treatment with the 2-hydroxypropyl-beta-cyclodextrin. In some cases, the treating results in an improvement in renal function as compared to renal function prior to treatment with the 2-hydroxypropyl-beta-cyclodextrin. In some cases, the treating results in an improvement in dermatologic manifestations as compared to prior to treatment. In some cases, the treating results in improvements in eosinophilia as compared to prior to treatment. In some cases, the treating results in improvements in hematologic abnormalities as compared to prior to treatment. In some cases, the treating results in improvements in complement levels as compared to prior to treatment. In some cases, the treating results in improvements in proteinuria as compared to prior to treatment.

In any one of the preceding aspects, therapeutically effective amount is from about 50 mg/kg to about 2,500 mg/kg. In any one of the preceding aspects, the therapeutically effective amount is from about 4 g to about 250 g. In any one of the preceding aspects, the therapeutically effective amount is an amount sufficient to achieve a serum, plasma, and/or whole blood concentration of 2-hydroxypropyl-beta-cyclodextrin of about 0.01 mM to about 3 mM. In any one of the preceding aspects, the 2-hydroxypropyl-beta-cyclodextrin is selected from the group consisting of: Kleptose® HP Parenteral Grade, Kleptose® HPB Parenteral Grade, Kleptose® HPB-LB Parenteral Grade, Cavitron® W7 HP5 Pharma cyclodextrin, Cavitron® W7 HP7 Pharma cyclodextrin, Trappsol® Cyclo™, and VTS-270/adrabetadex. In any one of the preceding aspects, the subject has one or more risk factors for CCE. In some cases, the one or more risk factors for CCE is selected from the group consisting of: interventional vascular procedures, interventional diagnostic procedures, cardiovascular surgery, cardiovascular disease (e.g., coronary artery disease, atherosclerotic cardiovascular disease), aortic aneurysm, aortic plaque, hypertension, diabetes mellitus, hyperlipidemia, smoking, being of the male sex, age, increased inflammation (e.g., increased serum (hs)CRP levels), anticoagulation, and thrombolytic treatment. In any one of the preceding aspects, the subject has one or more analytical lab results associated with CCE. In some cases, the one or more analytical lab results associated with CCE is selected from the group consisting of: increased serum creatinine, leukocytosis, eosinophilia, anemia, thrombocytopenia, hypocomplementemia, increased erythrocyte sedimentation rate, increased (hs)CRP levels, increased fibrinogen levels, eosinophiluria, proteinuria, hematuria, and abnormal liver enzymes. In any one of the preceding aspects, the individual is at least 30 (e.g., at least 40, at least 50, at least 60, at least 70, at least 80, at least 90) years old. In any one of the preceding aspects, the individual is a human. In any one of the preceding aspects, the administering further comprises: (i) administering, at a first time point, a therapeutically effective first dose of 2-hydroxypropyl-beta-cyclodextrin to the individual; and (ii) administering, at a second time point, a therapeutically effective second dose of 2-hydroxypropyl-beta-cyclodextrin to the individual. In any one of the preceding aspects, the second time point is at least 4 hours, at least 6 hours, at least 8 hours, at least 12 hours, at least 1 day, at least 2 days, at least 3 three days, at least 4 days, at least 5 days, at least 6 days, at least 1 week, at least 2 weeks, at least 3 weeks, or at least 4 weeks after the first time point. In any one of the preceding aspects, the administering is by intravenous administration.

In another aspect, a pharmaceutical composition is provided comprising: an amount of 2-hydroxypropyl-beta-cyclodextrin effective to reduce an amount of and/or a size of, and/or change a shape of circulating (e.g., blood, serum, plasma) cholesterol crystals (and/or clots comprising cholesterol crystals) in an individual; and a pharmaceutically acceptable excipient.

In another aspect, a pharmaceutical composition is provided comprising: an amount of 2-hydroxypropyl-beta-cyclodextrin effective treat cholesterol crystal embolization (CCE) and/or a symptom thereof, in an individual; and a pharmaceutically acceptable excipient.

In any one of the preceding aspects, the pharmaceutical composition is formulated for single dose administration. In any one of the preceding aspects, the pharmaceutical composition is formulated for intravenous administration.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1A:
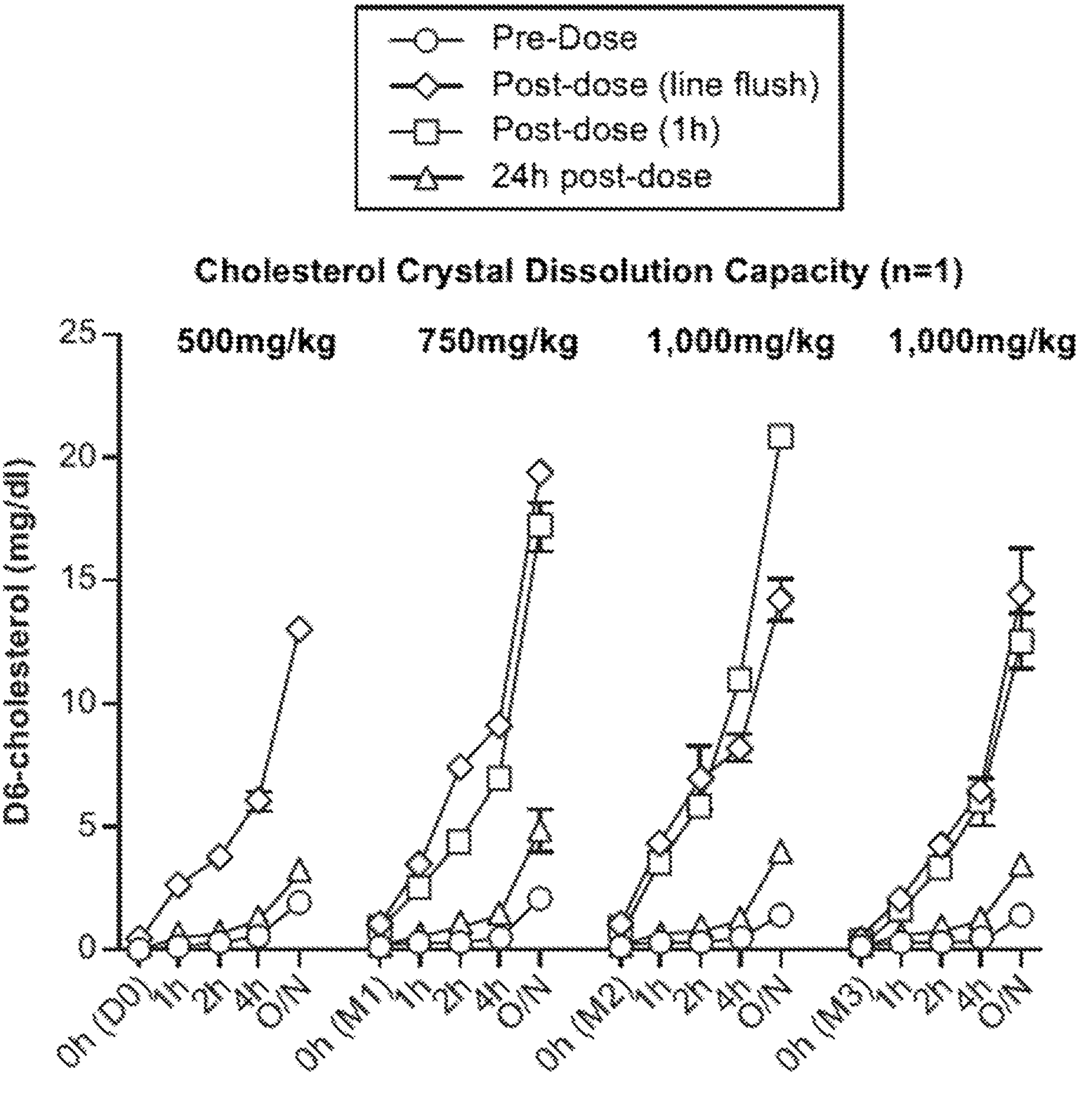
FIGS. 1A and 1B depict a non-limiting example of cholesterol crystal dissolution capacity (CCDC) of plasma obtained from a male human subject treated with increasing dosages of 2-hydroxypropyl-beta-cyclodextrin, in accordance with embodiments of the disclosure.

Disclosed herein are methods for reducing the amount of and/or the size of, and/or changing the shape of circulating (e.g., blood, plasma, serum) cholesterol crystals (and/or clots comprising cholesterol crystals) in an individual (e.g., a human). In some cases, the methods involve treating cholesterol crystal embolization (CCE) (e.g., by preventing the occlusion of small blood vessels by, e.g., cholesterol crystal emboli, cholesterol crystal clots, cholesterol crystal/protein clots, cholesterol crystal/DNA clots (e.g., extracellular traps), etc.). In some cases, the methods involve treating one or more symptom and/or clinical manifestation of CCE. In some cases, the methods involve treating ischemia to various organs and/or tissues caused by, e.g., CCE. Generally, the methods provided herein involve administering a therapeutically effective amount of a cyclodextrin to a subject in need thereof (e.g., a subject having elevated levels of circulating cholesterol crystals (and/or clots comprising cholesterol crystals)). In a particular aspect, the cyclodextrin is 2-hydroxypropyl-beta-cyclodextrin.

In some embodiments, disclosed herein are methods for preventing or reducing the risk of developing circulating (e.g., blood, plasma, serum) cholesterol crystals (and/or clots comprising cholesterol crystals) in an individual (e.g., a human). Further disclosed herein are methods for preventing or reducing the risk of an increase in the amount of and/or size of, and/or changing the shape of, circulating (e.g., blood, plasma, serum) cholesterol crystals (and/or clots comprising cholesterol crystals) in an individual (e.g., a human). In some cases, the methods involve preventing or reducing the risk of developing of cholesterol crystal embolization (CCE) (e.g., by preventing or reducing the risk of the occlusion of small blood vessels by, e.g., cholesterol crystal emboli, cholesterol crystal clots, cholesterol crystal/protein clots, cholesterol crystal/DNA clots (e.g., extracellular traps), etc.). In some cases, the methods involve preventing or reducing the risk of developing a symptom and/or a clinical manifestation of CCE. In some cases, the methods involve preventing or reducing the risk of ischemia to various organs and/or tissues caused by, e.g., CCE (and/or a symptom or clinical manifestation thereof, e.g., renal injury, atheroembolic renal disease (ARD)). Generally, the methods provided herein involve administering a therapeutically effective amount of a cyclodextrin to a subject in need thereof (e.g., prophylactically, e.g., to a subject at risk of developing CCE). In a particular aspect, the cyclodextrin is 2-hydroxypropyl-beta-cyclodextrin.

In some embodiments, disclosed herein are methods for the treatment of cardiovascular disease. In some cases, the cardiovascular disease is atherosclerotic cardiovascular disease (e.g., cardiovascular disease caused or contributed to by atherosclerosis). The atherosclerotic cardiovascular disease may be any one of coronary artery disease (CAD), stroke, peripheral artery disease (PAD), peripheral vascular diseases (PVD), chronic kidney disease (CKD) caused by atherosclerosis, end-stage kidney disease (ESKD) caused by atherosclerosis, acute kidney failure caused by atherosclerosis, atherosclerotic renovascular disease (ARVD), renal artery stenosis, aortic aneurysm, idiopathic peripheral atrial hypertension, erectile dysfunction, intermittent claudication, and/or post-surgical or iatrogenic arterial disease. In some cases, PAD includes lower extremity arterial disease. In some cases, the methods involve treating and/or preventing atherosclerosis. In some cases, the methods involve treating a subject who has, is suspected of having, or is at risk of developing acute coronary syndrome (ACS) or chronic coronary syndrome (CCS) (e.g., as defined by the European Society of Cardiology). In some aspects, the methods may involve administering a therapeutically effective amount of a cyclodextrin to a subject in need thereof (e.g., a subject having, suspected of having, or at risk of developing cardiovascular disease (e.g., atherosclerotic cardiovascular disease)). In some cases, the therapeutically effective amount is an amount effective to increase a circulating and/or systemic level of one or more sterol and/or oxysterol in the subject compared to a baseline (e.g., pre-treatment with cyclodextrins). In a particular aspect, the cyclodextrin is 2-hydroxypropyl-beta-cyclodextrin.

The below terms are discussed to illustrate meanings of the terms as used in this specification, in addition to the understanding of these terms by those of skill in the art. As used herein and in the appended claims, the singular forms "a," "an," and, "the" include plural referents unless the context clearly dictates otherwise. It is further noted that the claims can be drafted to exclude any optional element. As such, this statement is intended to serve as antecedent basis for use of such exclusive terminology as "solely," "only," and the like in connection with the recitation of claim elements, or use of a "negative" limitation.

As used herein, the term "about" a number refers to that number plus or minus 10% of that number. The term "about" a range refers to that range minus 10% of its lowest value and plus 10% of its greatest value.

As used herein, the terms "subject", "individual", and "patient" are used interchangeably. None of the terms are to be interpreted as requiring the supervision of a medical professional (e.g., a doctor, nurse, physician's assistant, orderly, hospice worker). As used herein, the subject may be any animal, including mammals (e.g., a human or non-human animal) and non-mammals. In one embodiment, the subject is a human.

As used herein, the terms "treat", "treating", or "treatment", and other grammatical equivalents, include ameliorating or preventing the underlying causes of one or more symptoms of a disease or condition; alleviating, abating, or ameliorating one or more symptoms of a disease or condition; ameliorating, preventing, or reducing the appearance, severity, or frequency of one or more symptoms of a disease or condition; inhibiting the disease or condition, such as, for example, arresting the development of the disease or condition, relieving the disease or condition, causing regression of the disease or condition, relieving a condition caused by the disease or condition, or inhibiting the symptoms of the disease or condition either prophylactically and/or therapeutically. Methods of treatment as disclosed herein include disclosures of the use of the (e.g., pharmaceutical) compositions provided herein for the treatment of any indication described herein, and include disclosures of the (e.g., pharmaceutical) compositions provided herein for the use in treating any indication described herein.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use. "Pharmaceutically acceptable" can refer to a material, such as a carrier, or diluent, which does not abrogate the biological activity or properties of the compound, and is relatively nontoxic, e.g., the material may be administered to an individual without causing undesirable biological effects or interacting in a deleterious manner with any of the components of the composition in which it is contained.

"Pharmaceutically acceptable excipient" as used herein, refers to any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents, excipients, preservatives, or lubricants used in formulating pharmaceutical products.

The terms "effective amount" or "therapeutically effective amount", as used herein, refer to a sufficient amount of an agent or a compound being administered which relieves, to some extent, one or more of the symptoms of the disease or condition being treated, or reduces the underlying cause of the disease or condition being treated. In some embodiments, the result is a reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms or underlying cause of the disease (e.g., without undue adverse side effects). In some embodiments, an appropriate "effective amount" in any individual case is determined using techniques, such as a dose escalation study. The term "therapeutically effective amount" includes, for example, a prophylactically effective amount. An "effective amount" of a compound disclosed herein may be an amount effective to achieve a desired effect or therapeutic improvement (e.g., without undue adverse side effects). An "effective amount" of a compound disclosed herein may be an amount effective to achieve one or more desired outcomes. It should be understood that, in some cases, "an effective amount" or "a therapeutically effective amount" varies from subject to subject, due to variation in metabolism of the composition, age, weight, general condition of the subject, concomitant medications the subject may be taking, the condition being treated, the severity of the condition being treated, and the judgment of the prescribing physician. In some instances, the disease or condition being treated is CCE. In some instances, the disease or condition being treated is a disease or condition associated with or caused by CCE.

Methods of Treating Cholesterol Crystal Embolization and Symptoms Thereof

Examples 1-3 herein depict data demonstrating increased plasma cholesterol crystal dissolution capacity, increased oxysterol levels, and increased mRNA levels of the LXR transcription factor-regulated genes ABCA1 and ABCG1 in a human subject treated with 2-hydroxypropyl-beta-cyclodextrin. The data suggests that 2-hydroxypropyl-beta-cyclodextrin may be used to treat cholesterol crystal embolization (CCE) as described herein.

Accordingly, disclosed herein are methods for treating a subject having, suspected of having, or at risk of developing CCE or a symptom and/or clinical manifestation thereof (e.g., by reducing an amount and/or size of circulating cholesterol crystals (and/or clots comprising cholesterol crystals), and/or changing a shape of circulating cholesterol crystals (and/or clots comprising cholesterol crystals)). In some cases, the symptom and/or clinical manifestation thereof is one or more cutaneous manifestations of CCE. The one or more cutaneous manifestations of CCE include, without limitation, livedo reticularis (e.g., purple discoloration of the skin), cyanosis (e.g., a bluish discoloration of the skin resulting from poor circulation or inadequate oxygenation of the blood), gangrene (e.g., death of body tissue due to a lack of blood flow), skin ulcers, purpura, erythematous nodules, and blue-toe syndrome. In some cases, the symptom or clinical manifestation thereof is atheroembolic renal disease. In some cases, the symptom or clinical manifestation thereof is one or more renal manifestations of CCE. The one or more renal manifestations of CCE include, without limitation, acute kidney injury, subacute kidney injury, chronic kidney injury, malignant hypertension, glomerulonephritis, end-stage renal disease, renal allograft dysfunction, and renal infarction. In some cases, the symptom or clinical manifestation thereof is one or more gastrointestinal manifestations of CCE. The one or more gastrointestinal manifestations of CCE include, without limitation, abdominal pain, diarrhea, bleeding, bowel ischemia, bowel infarction, bowel perforation, necrotizing pancreatitis, focal hepatic cell necrosis, and acalculous cholecystitis. In some cases, the symptom or clinical manifestation thereof is one or more central nervous system manifestations of CCE. The one or more central nervous system manifestations of CCE include, without limitation, headache, dizziness, confusion, memory loss, transient ischemic attack, stroke, cerebral infarction, spinal cord infarction, paraparesis, and mononeuropathy. In some cases, the symptom or clinical manifestation thereof is one or more ocular manifestation of CCE. The one or more ocular manifestations of CCE include, without limitation, amaurosis fugax, eye pain, blurred vision, and Hollenhorst plaques. In some cases, the symptom or clinical manifestation thereof is one or more of the following: myocardial infarction, adrenal insufficiency, penile necrosis, myositis, rhabdomyolysis, splenic infarcts, and alveolar hemorrhage. In some cases, the symptom or clinical manifestation thereof is one or more of, without limitation, fever, fatigue, anorexia, weight loss, and myalgia.

In some cases, treating a subject as described herein reduces the size (e.g., average size, maximum size) of circulating (e.g., blood, plasma, serum) cholesterol crystals (and/or clots comprising cholesterol crystals) in the subject. In some cases, the size (e.g., average size, maximum size) of circulating (e.g., blood, serum, plasma) cholesterol crystals (and/or clots comprising cholesterol crystals) is reduced by at least about 10% (e.g., at least about 15%, at least about 20%, at least about 25%, at least about 30%, at least about 35%, at least about 40%, at least about 45%, at least about 50%, or greater) relative to the size (e.g., average size, maximum size) of circulating (e.g., blood, serum, plasma) cholesterol crystals (and/or clots comprising cholesterol crystals) prior to treatment with the 2-hydroxypropyl-beta-cyclodextrin. In some cases, treating a subject as described herein reduces an amount (e.g., concentration) of circulating (e.g., blood, plasma, serum) cholesterol crystals (and/or clots comprising cholesterol crystals) in the subject. In some cases, the amount (e.g., concentration) of circulating (e.g., blood, serum, plasma) cholesterol crystals (and/or clots comprising cholesterol crystals) is reduced by at least about 10% (e.g., at least about 15%, at least about 20%, at least about 25%, at least about 30%, at least about 35%, at least about 40%, at least about 45%, at least about 50%, or greater) relative to the amount (e.g., concentration) of circulating (e.g., blood, serum, plasma) cholesterol crystals (and/or clots comprising cholesterol crystals) prior to treatment with the 2-hydroxypropyl-beta-cyclodextrin. In some cases, treating a subject as described herein leads to dissolution of circulating (e.g., blood, plasma, serum) cholesterol crystals (and/or clots comprising cholesterol crystals) in the subject. In some cases, treating a subject as described herein results in a change in shape of circulating cholesterol crystals (and/or clots comprising cholesterol crystals). In some cases, reducing the number and/or size, and/or changing the shape of circulating cholesterol crystals (and/or clots comprising cholesterol crystals) in the subject ameliorates or reduces CCE in the subject. In some cases, reducing the number and/or size, and/or changing the shape of circulating cholesterol crystals (and/or clots comprising cholesterol crystals) in the subject ameliorates or reduces one or more symptoms and/or clinical manifestations of CCE in the subject. In some cases, treating a subject as described herein results in a decrease in inflammation (e.g., as measured by, e.g., cytokine protein and/or RNA levels) as compared to a level of inflammation prior to treatment with the 2-hydroxypropyl-beta-cyclodextrin. In some cases, treating a subject as described herein results in an improvement in renal function as compared to renal function prior to treatment with the 2-hydroxypropyl-beta-cyclodextrin. In some cases, treating a subject as described herein results in an improvement in dermatologic manifestations as compared to prior to treatment with the 2-hydroxypropyl-beta-cyclodextrin. In some cases, treating a subject as described herein results in improvements in eosinophilia as compared to prior to treatment with the 2-hydroxypropyl-beta-cyclodextrin. In some cases, treating a subject as described herein results in improvements in hematologic abnormalities as compared to prior to treatment with the 2-hydroxypropyl-beta-cyclodextrin. In some cases, treating a subject as described herein results in improvements in complement levels as compared to prior to treatment with the 2-hydroxypropyl-beta-cyclodextrin. In some cases, treating a subject as described herein results in improvements in proteinuria as compared to prior to treatment with the 2-hydroxypropyl-beta-cyclodextrin.

In various aspects, the methods involve administering a cyclodextrin to a subject (e.g., having, suspected of having, or at risk of developing CCE and/or one or more diseases or conditions associated therewith). Cyclodextrins are a family of cyclic oligosaccharides, consisting of a cyclic (e.g., macrocyclic) ring of glucose subunits joined by α-1,4 glycosidic bonds. Cyclodextrins contain a number of glucose monomers in a ring formation. Common cyclodextrins include alpha-cyclodextrins (consisting of six glucose monomers), beta-cyclodextrins (consisting of seven glucose monomers), gamma-cyclodextrins (consisting of eight glucose monomers), and delta-cyclodextrins (consisting of nine glucose monomers). The outer portion of the ring structure is hydrophilic and the inner cavity of the ring structure is hydrophobic; thus, cyclodextrins generally are water soluble (e.g., due to the hydrophilic exterior), and capable of incorporating hydrophobic molecules in the cavity (e.g., due to the hydrophobic cavity). Parent cyclodextrins have limited water solubility; therefore, several chemically modified cyclodextrins have been synthesized where the hydroxyl groups are substituted with other chemical moieties to, e.g., increase solubility. In various aspects, the methods provided herein involve administering a cyclodextrin to a subject (e.g., a human) in need thereof (e.g., having an elevated amount of circulating cholesterol crystals (and/or clots comprising cholesterol crystals); e.g., having, suspected of having, or at risk of developing CCE). In some cases, the subject has, is suspected of having, or is at risk of developing circulating cholesterol crystals (and/or clots comprising cholesterol crystals) or elevated levels of circulating cholesterol crystals (and/or clots comprising cholesterol crystals) (e.g., after rupture of an atherosclerotic plaque).

In particular embodiments, the cyclodextrin is 2-hydroxypropyl-beta-cyclodextrin. In some instances, the 2-hydroxypropyl-beta-cyclodextrin is selected from the group consisting of: Kleptose® HP Parenteral Grade (Roquette Frères, #346114; accessible at roquette.com/-/media/roquette-sharepoint-libraries/sdol_product-specification-sheet/roquette_quality_specification-sheet_kleptose-hp-parenteral-grade 50_346114_en.pdf as of Aug. 26, 2020), Kleptose® HPB Parenteral Grade (Roquette Frères, #346111; accessible at roquette.com/-/media/roquette-sharepoint-libraries/sdol_product-specification-sheet/roquette_quality_specification-sheet_kleptose-hpb-parenteral-grade_50_346111_en.pdf as of Aug. 26, 2020), Kleptose® HPB-LB Parenteral Grade (Roquette Frères, #346115; accessible at roquette.com/-/media/roquette-sharepoint-libraries/sdol_product-specification-sheet/roquette_quality_specification-sheet_kleptose-hpb-lb-parenteral-grade_50_346115_en.pdf as of Aug. 26, 2020), Cavitron® W7 HP5 Pharma cyclodextrin (Ashland; accessible at ashland.com/file_source/Ashland/Product/Documents/Pharmaceutical/PC_11734_Cavitron_Cav asol.pdf as of Aug. 26, 2020), Cavitron® W7 HP7 Pharma cyclodextrin (Ashland; accessible at ashland.com/file_source/Ashland/Product/Documents/Pharmaceutical/PC_11734_Cavitron_Cav asol.pdf as of Aug. 26, 2020), Trappsol® Cyclo™ (Cyclo Therapeutics, Inc.; accessible at cyclotherapeutics.com/cyclodextrins/trappsol-cyclo as of Aug. 26, 2020), and VTS-270/adrabetadex.

In certain embodiments, a cyclodextrin provided or used in a (e.g., pharmaceutical) composition or method or other application herein is a mixture of cyclodextrins; for example, in some embodiments, a 2-hydroxypropyl-beta-cyclodextrin provided herein comprises a mixture of 2-hydroxypropyl-beta-cyclodextrins. In some embodiments, a cyclodextrin molecule provided herein is optionally substituted with one or more chemical group, each chemical group independently being a hydroxypropyl group, a hydroxyethyl group, a methyl group, an ethyl group, a carboxymethyl group, a heptakis(2,6-di-O-methyl) group, a sulfoethyl group, a sulfopropyl group, and/or a sulfobutyl ethyl group, or its oligomer thereof. In some preferred embodiments, the cyclodextrin is a hydroxypropyl-beta-cyclodextrin, such as wherein one or more hydroxyl of the cyclodextrin is substituted with hydroxypropyl (e.g., 2-hydroxypropyl group). For example, one or more hydroxyl positions are substituted by one or more hydroxypropyl groups by substituting the H of the hydroxyl (OH) with a $—CH_2CH_2(OH)CH_3$ group, such as illustrated in Formula I below. In some embodiments, the 2-hydroxypropyl-beta-cyclodextrin comprises a plurality of cyclodextrins with various different Degree of Substitution (DS) values and/or having a Molar Substitution (MS) value.

Formula I

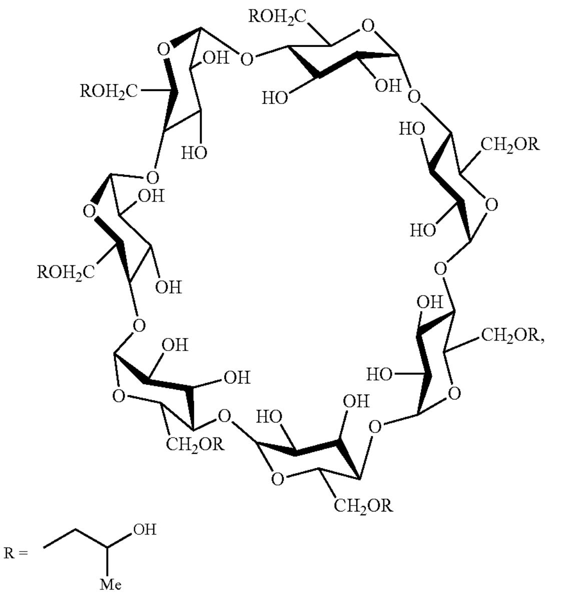

wherein each R is independently H or as noted above, and wherein at least one R is not H.

In some embodiments, the plurality of beta-cyclodextrin molecules in a beta-cyclodextrin (mixture of beta-cyclodextrin molecules) is characterized by an average molar substitution. The "molar substitution," or "MS," is the average number of substituents per glucose unit in the beta-cyclodextrin molecules. In some embodiments, MS is determined according to the procedures set forth in the USP monograph on Hydroxypropyl Betadex (USP NF 2015) ("USP Hydroxypropyl Betadex monograph"), incorporated herein by reference in its entirety. In some embodiments, the (e.g., pharmaceutical) compositions provided herein contain a plurality of beta-cyclodextrin molecules having an average MS of at least about 0.3. In some embodiments, the (e.g., pharmaceutical) compositions provided herein contain a plurality of beta-cyclodextrin molecules having an average MS of about 0.3 to 1.0.

In some embodiments, the plurality of beta-cyclodextrin molecules is characterized by average degree of substitution. The term "degree of substitution," or "DS," refers to the total number of substituents substituted directly or indirectly on a beta-cyclodextrin molecule. In some embodiments, the beta-cyclodextrin molecule may have one, or multiple, glucose units that are substituted by a substituent at a hydroxyl position. Thus, average DS refers to the total number of substituents in a population of beta-cyclodextrins divided by the number of beta-cyclodextrin molecules. In some embodiments, the average DS of the molecule is measured using Electron Spray Ionization-Mass Spectrometry (ESI-MS) analysis (e.g., HPLC-ESI-MS, etc.). In some embodiments, the average DS of the molecule is determined by peak heights of an electrospray MS spectrum. In some embodiments, the average DS of the molecule is determined by multiplying the MS by 7. In some embodiments, the (e.g., pharmaceutical) compositions provided herein contain a plurality of beta-cyclodextrin molecules having an average DS of about 2.0 to 7.0

In some embodiments, any atom of the cyclodextrins described herein (e.g., 2-hydroxypropyl-beta-cyclodextrin) may be substituted with any suitable isotope. In a particular embodiment, any one or more hydrogen atoms of the cyclodextrins described herein (e.g., 2-hydroxypropyl-beta-cyclodextrin) may be substituted or replaced with deuterium atoms. Such cyclodextrins are expected to have similar or improved properties as compared to the original cyclodextrin that does not contain deuterium. Deuterium is a safe, stable, non-radioactive isotope of hydrogen. Compared to hydrogen, deuterium forms stronger bonds with carbon. In some instances, the increased bond strength imparted by deuterium can positively impact properties of the cyclodextrins, creating the potential for improved drug efficacy, safety, and/or tolerability. In addition, deuteration may cause decreased metabolic clearance in vivo, thereby increasing the half-life and circulation of the compound. At the same time, because the size and shape of deuterium are essentially identical to those of hydrogen, replacement of hydrogen by deuterium would not be expected to affect the biochemical potency and selectivity of the compound as compared to the original chemical entity that contains only hydrogen.

In various aspects, a therapeutically effective amount of 2-hydroxypropyl-beta-cyclodextrin is administered to the subject. In some embodiments, administration of a therapeutically effective amount of 2-hydroxypropyl-beta-cyclodextrin increases a circulating and/or systemic level of one or more derivative of cholesterol as compared to a baseline. In some embodiments, the one or more derivative of cholesterol is a by-product of cholesterol biosynthesis. In some embodiments, the one or more derivative of cholesterol comprises a hydrogenated product, products with differently hydrogenated 1H-cyclopenta[a]phenanthren-3-ol products, or products formed with a hydroxyl, epoxyl, or keto group. In some cases, the one or more derivative of cholesterol is an oxysterol or a sterol.

In some embodiments, the therapeutically effective amount of 2-hydroxypropyl-beta-cyclodextrin is an amount suitable to achieve the therapeutic effect described herein. In some embodiments, the therapeutically effective amount is at least about 50 mg/kg, at least about 100 mg/kg, at least about 200 mg/kg, at least about 300 mg/kg, at least about 400 mg/kg, at least about 500 mg/kg, at least about 600 mg/kg, at least about 700 mg/kg, at least about 800 mg/kg, at least about 900 mg/kg, at least about 1000 mg/kg, at least about 1100 mg/kg, at least about 1200 mg/kg, at least about 1300 mg/kg, at least about 1400 mg/kg, at least about 1500 mg/kg, at least about 1600 mg/kg, at least about 1700 mg/kg, at least about 1800 mg/kg, at least about 1900 mg/kg, at least about 2000 mg/kg, at least about 2100 mg/kg, at least about 2200 mg/kg, at least about 2300 mg/kg, at least about 2400 mg/kg, or at least about 2500 mg/kg. In some embodiments, the therapeutically effective amount of 2-hydroxypropyl-beta-cyclodextrin is at least about 100 mg/kg. In some embodiments, the therapeutically effective amount of 2-hydroxypropyl-beta-cyclodextrin is at least about 250 mg/kg. In some embodiments, the therapeutically effective amount of 2-hydroxypropyl-beta-cyclodextrin is at least about 500 mg/kg. In some embodiments, the therapeutically effective amount of 2-hydroxypropyl-beta-cyclodextrin is at least about 1000 mg/kg. In some embodiments, the therapeutically effective amount of 2-hydroxypropyl-beta-cyclodextrin is at least about 1500 mg/kg.

In some embodiments, the therapeutically effective amount of 2-hydroxypropyl-beta-cyclodextrin is an amount suitable to achieve the therapeutic effect described herein. In some embodiments, the therapeutically effective amount is from about 50 mg/kg to about 2500 mg/kg (e.g., from about 50 mg/kg to about 1000 mg/kg, from about 500 mg/kg to about 1000 mg/kg, from about 500 mg/kg to about 1500 mg/kg, from about 800 mg/kg to about 1500 mg/kg, from about 800 mg/kg to about 1200 mg/kg, from about 1000 mg/kg to about 1500 mg/kg, from about 1000 mg/kg to about 2500 mg/kg. In some embodiments, the therapeutically effective amount of 2-hydroxypropyl-beta-cyclodextrin is from about 500 mg/kg to about 1500 mg/kg. In some embodiments, the therapeutically effective amount of 2-hydroxypropyl-beta-cyclodextrin is from about 800 mg/kg to about 1200 mg/kg.

In some embodiments, the therapeutically effective amount of 2-hydroxypropyl-beta-cyclodextrin is an amount suitable for achieving the therapeutic effect described herein. In some embodiments, the therapeutically effective amount is at least about 4 g (e.g., at least about 10 g, at least about 25 g, at least about 50 g, at least about 75 g, at least about 100 g, at least about 125 g, at least about 150 g, at least about 175 g, at least about 200 g, at least about 250 g). In some embodiments, the therapeutically effective amount of 2-hydroxypropyl-beta-cyclodextrin may be from about 4 g to about 250 g (e.g., from about 4 g to about 200 g, from about 4 g to about 150 g, from about 4 g to about 100 g, from about 4 g to about 50 g, from about 50 g to about 250 g, from about 50 g to about 200 g, from about 50 g to about 150 g, from about 50 g to about 100 g, from about 100 g to about 250 g, from about 100 g to about 200 g). The total amount of 2-hydroxpropyl-beta-cyclodextrin administered (e.g., in a single dose administration, e.g., in a therapeutically effective amount) may depend on a number of factors, including, without limitation, the subject's age, gender, weight, and the like.

In some embodiments, the therapeutically effective amount of 2-hydroxypropyl-beta-cyclodextrin is an amount sufficient to achieve a whole blood, serum, and/or plasma concentration of 2-hydroxypropyl-beta-cyclodextrin suitable for achieving the therapeutic effect described herein. In some embodiments, the whole blood, serum, and/or plasma concentration is at least about 0.01 mM (e.g., at least about 0.05 mM, at least about 0.1 mM, at least about 0.2 mM, at least about 0.3 mM, at least about 0.4 mM, at least about 0.5 mM, at least about 0.6 mM, at least about 0.7 mM, at least about 0.8 mM, at least about 0.9 mM, at least about 1.0 mM, at least about 1.5 mM, at least about 2.0 mM, at least about 2.5 mM, or at least about 3 mM).

A therapeutically effective amount may be an amount of 2-hydroxypropyl-beta-cyclodextrin effective to increase a circulating and/or systemic level of one or more oxysterol in the individual after the administering as compared to prior to the administering. In some cases, the therapeutically effective amount is an amount of 2-hydroxypropyl-beta-cyclodextrin effective to increase a circulating and/or systemic level of one or more oxysterol in the individual by at least about 10% (e.g., at 1 hour after the administering) as compared to prior to the administering, such as by at least about 15%, at least about 20%, at least about 25%, at least about 30%, at least about 35%, at least about 40%, at least about 45%, at least about 50%, or greater. In some embodiments, the one or more oxysterol is 24S-hydroxycholesterol, 27-hydroxycholesterol, or both.

A therapeutically effective amount may be an amount of 2-hydroxypropyl-beta-cyclodextrin effective to increase plasma cholesterol crystal dissolution capacity (CCDC) after the administering (e.g., 1 hour after the administering) as compared to prior to the administering. In some cases, the therapeutically effective amount is an amount of 2-hydroxypropyl-beta-cyclodextrin effective to increase plasma CCDC by at least about 10% (e.g., at 1 hour) after the administering as compared to prior to the administering, such as by at least about 15%, at least about 20%, at least about 25%, at least about 30%, at least about 35%, at least about 40%, at least about 45%, at least about 50%, or greater.

A therapeutically effective amount may be an amount of 2-hydroxypropyl-beta-cyclodextrin effective to increase mRNA levels of one or more LXR transcription factor-regulated genes (e.g., ABCA1, ABCG1) after the administering (e.g., 24 hours after the administering) as compared to prior to the administering. In some cases, the therapeutically effective amount is an amount of 2-hydroxypropyl-beta-cyclodextrin effective to increase mRNA levels of ABCA1 and/or ABCG1 by at least about 10% (e.g., at 24 hours) after the administering as compared to prior to the administering, such as by at least about 15%, at least about 20%, at least about 25%, at least about 30%, at least about 35%, at least about 40%, at least about 45%, at least about 50%, or greater.

The methods disclosed herein may further comprise administering, at a first time point, a therapeutically effective first amount of 2-hydroxypropyl-beta-cyclodextrin to a subject, and administering, at a second time point, a therapeutically effective second amount of 2-hydroxypropyl-beta-cyclodextrin to the subject. The second time point can be at least 4 hours, at least 6 hours, at least 8 hours, at least 12 hours, at least 1 day, at least 2 days, at least 3 days, at least 4 days, at least 5 days, at least 6 days, at least 1 week, at least 2 weeks, at least 3 weeks, or at least 4 weeks after the first time point. In some embodiments, the administering may be by intravenous administration.

In some cases, the second time point may be determined based on one or more indicators that an additional dose of drug would be beneficial to the subject. For example, the second time point may be administered after the therapeutic benefit of the first dose has diminished or has started to diminish.

In various aspects, the subject can be a human. In some cases, the subject may be of any age that is at risk of or more prone to developing elevated levels of circulating cholesterol crystals (and/or clots comprising cholesterol crystals) and/or CCE. The subject may be at least 30 years old (e.g., at least 40, at least 50 at least 60, at least 70, at least 80, at least 90 years old). The subject can be diagnosed with atherosclerosis and/or atherosclerotic cardiovascular disease. In some cases, the subject has advanced atherosclerosis. In some cases, the subject has undergone a medical procedure involving the blood vessels, such as vascular surgery or angiography. In some cases, the subject has commenced treatment with an anticoagulant or a thrombolytic medication. The subject may have one or more risk factors for CCE. Risk factors for CCE include, but are not limited to, interventional vascular procedures, interventional diagnostic procedures, cardiovascular surgery, cardiovascular disease (e.g., coronary artery disease, atherosclerotic cardiovascular disease), aortic aneurysm, aortic plaque, hypertension, diabetes mellitus, hyperlipidemia, smoking, being of the male sex, age, increased inflammation (e.g., increased serum (hs)CRP levels), anticoagulation, and thrombolytic treatment.

The subject can be diagnosed with CCE and/or may have a symptom and/or a clinical manifestation of CCE. CCE can be diagnosed by, e.g., a biopsy (e.g., a skin biopsy, a muscle biopsy, a kidney biopsy, bone marrow biopsy, gastric mucosa biopsy, colonic mucosa biopsy). In some cases, the subject can be diagnosed by a combination of an inciting event (e.g., cardiovascular surgery) and characteristic manifestations of the disease (e.g., cutaneous, renal, central nervous system, ocular manifestations (e.g., Hollenhorst plaques), e.g., as described herein). In some cases, the subject can be diagnosed by a non-invasive imaging modality (e.g., abdominal ultrasound, chest/abdominal computerized tomography (CT), transthoracic echocardiogram (TTE), transesophageal echocardiogram (TEE)).

The subject can have one or more analytical laboratory results consistent with CCE. The one or more analytical laboratory results consistent with CCE may include, without limitation, increased serum creatinine, leukocytosis, eosinophilia, anemia, thrombocytopenia, hypocomplementemia, increased erythrocyte sedimentation rate, increased (hs)CRP levels, increased fibrinogen levels, eosinophiluria, proteinuria, hematuria, and abnormal liver enzymes.

The subject may be treated (e.g., by the methods described herein) before developing CCE (e.g., after an inciting event, e.g., cardiovascular surgery). For example, a subject at risk of developing CCE (e.g., a subject with elevated levels of circulating cholesterol crystals (and/or clots comprising cholesterol crystals)) may be treated (e.g., by the methods described herein), e.g., to decrease the amount and/or size of, and/or change the shape of the circulating cholesterol crystals (and/or clots comprising cholesterol crystals) (e.g., thereby reducing the risk of developing CCE). In some cases, a subject having one or more risk factors for CCE is treated prior to developing elevated levels of circulating cholesterol crystals (and/or clots comprising cholesterol crystals). The subject may be treated (e.g., by the methods described herein) after developing CCE and/or a symptom or clinical manifestation thereof.

The methods disclosed herein can be used to treat CCE and/or one or more symptoms and/or clinical manifestations thereof. For example, the methods disclosed herein can be used to treat cutaneous manifestations of CCE (e.g., livedo reticularis, cyanosis, gangrene, skin ulcers, purpura, erythematous nodules, blue-toe syndrome); atheroembolic renal disease and/or renal manifestations of CCE (e.g., acute kidney injury, subacute kidney injury, chronic kidney injury, malignant hypertension, glomerulonephritis, end-stage renal disease, renal allograft dysfunction, renal infarction), gastrointestinal manifestations of CCE (e.g., abdominal pain, diarrhea, bleeding, bowel ischemia, bowel infarction, bowel perforation, necrotizing pancreatitis, focal hepatic cell necrosis, acalculous cholecystitis), central nervous system manifestations of CCE (e.g., headache, dizziness, confusion, memory loss, transient ischemic attack, stroke, cerebral infarction, spinal cord infarction, paraparesis, mononeuropathy), ocular manifestations of CCE (e.g., amaurosis fugax, eye pain, blurred vision, Hollenhorst plaques), myocardial infarction, adrenal insufficiency, penile necrosis, myositis, rhabdomyolysis, splenic infarcts, alveolar hemorrhage; and/or symptoms associated with CCE (e.g., fever, fatigue, anorexia, weight loss, myalgia).

In some embodiments, the methods described herein cause a reduction in the size (e.g., average size, maximum size) of circulating (e.g., blood, plasma, serum) cholesterol crystals (and/or clots comprising cholesterol crystals) in the subject. In some cases, the size (e.g., average size, maximum size) of circulating (e.g., blood, plasma, serum) cholesterol crystals (and/or clots comprising cholesterol crystals) may be reduced relative to the size (e.g., average size, maximum size) of the circulating (e.g., blood, plasma, serum) cholesterol crystals (and/or clots comprising cholesterol crystals) prior to the treating. In some embodiments, the size (e.g., average size, maximum size) of circulating (e.g., blood, plasma, serum) cholesterol crystals (and/or clots comprising cholesterol crystals) may be reduced by at least about 0.5%. In some embodiments, the size (e.g., average size, maximum size) of circulating (e.g., blood, plasma, serum) cholesterol crystals (and/or clots comprising cholesterol crystals) may be reduced by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or greater.

In some embodiments, the methods described herein causes a reduction in the amount (e.g., concentration) of circulating (e.g., blood, plasma, serum) cholesterol crystals (and/or clots comprising cholesterol crystals) in the subject. In some cases, the amount (e.g., concentration) of circulating (e.g., blood, plasma, serum) cholesterol crystals (and/or clots comprising cholesterol crystals) may be reduced relative to the amount (e.g., concentration) of circulating (e.g., blood, plasma, serum) cholesterol crystals (and/or clots comprising cholesterol crystals) prior to the treating. In some embodiments, the amount (e.g., concentration) of circulating (e.g., blood, plasma, serum) cholesterol crystals (and/or clots comprising cholesterol crystals) may be reduced by at least about 0.5%. In some embodiments, the amount (e.g., concentration) of circulating (e.g., blood, plasma, serum) cholesterol crystals (and/or clots comprising cholesterol crystals) may be reduced by at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or greater. In some embodiments, the methods described herein result in a change in the shape of circulating cholesterol crystals (and/or clots comprising cholesterol crystals).

In some cases, the methods described herein cause a decrease in inflammation (e.g., as measured by, e.g., cytokine protein and/or RNA levels) as compared to a level of inflammation prior to treatment with the 2-hydroxypropyl-beta-cyclodextrin. In some cases, the methods described herein cause an improvement in renal function as compared to renal function prior to treatment with the 2-hydroxypropyl-beta-cyclodextrin. In some cases, the methods described herein result in an improvement in dermatologic manifestations as compared to prior to treatment with the 2-hydroxypropyl-beta-cyclodextrin. In some cases, the methods as described herein result in improvements in eosinophilia as compared to prior to treatment with the 2-hydroxypropyl-beta-cyclodextrin. In some cases, the methods as described herein result in improvements in hematologic abnormalities as compared to prior to treatment with the 2-hydroxypropyl-beta-cyclodextrin. In some cases, the methods as described herein result in improvements in complement levels as compared to prior to treatment with the 2-hydroxypropyl-beta-cyclodextrin. In some cases, the methods as described herein result in improvements in proteinuria as compared to prior to treatment with the 2-hydroxypropyl-beta-cyclodextrin.

In some embodiments, the methods involve treating a subject (e.g., having, suspected of having, or at risk of developing CCE) with a combination of 2-hydroxypropyl-beta-cyclodextrin and an additional therapeutic.

In some cases, the additional therapeutic is selected from the group consisting of: a HMG-CoA reductase inhibitor (statin), an anti-inflammatory drug (e.g., acetyl salicylic acid, colchicine, canakinumab), a corticosteroid, an immunosuppressive drug (e.g., cyclophosphamide), and a proprotein convertase subtilisin/kexin type 9 (PCSK9) inhibitor.

In some cases, 2-hydroxypropyl-beta-cyclodextrin and the additional therapeutic are administered to the subject at or near the same time (e.g., in a single formulation, or as separate formulations). In some cases, 2-hydroxypropyl-beta-cyclodextrin and the additional therapeutic are administered at different times (e.g., in separate formulations). In some cases, the additional therapeutic is administered prior to administration with 2-hydroxypropyl-beta-cyclodextrin. In some cases, the additional therapeutic is administered concurrently with 2-hydroxypropyl-beta-cyclodextrin. In some cases, the additional therapeutic is administered after administration of 2-hydroxypropyl-beta-cyclodextrin.

In some cases, the subject may have previously been undergoing treatment with an additional therapeutic (e.g., prior to administration with 2-hydroxypropyl-beta-cyclodextrin). In some cases, the treatment with the additional therapeutic may be ineffective or may have limited efficacy. In such cases, subjects treated with 2-hydroxypropyl-beta-cyclodextrin (e.g., after treatment with the additional therapeutic, or concurrently with the additional therapeutic) may exhibit a greater therapeutic benefit than administration of the additional therapeutic alone.

In some cases, subjects treated with both 2-hydroxypropyl-beta-cyclodextrin and an additional therapeutic may exhibit a therapeutic benefit greater than the therapeutic benefit exhibited by treatment with either the additional therapeutic or the 2-hydroxypropyl-beta-cyclodextrin alone. In some cases, treatment with both the additional therapeutic and 2-hydroxypropyl-beta-cyclodextrin has a synergistic effect, such that the interaction between the additional therapeutic and 2-hydroxypropyl-beta-cyclodextrin causes the total effect of the therapeutics to be greater than the sum of the individual effects of each therapeutic. In some cases, treatment with both the additional therapeutic and 2-hydroxypropyl-beta-cyclodextrin has an additive effect.

Pharmaceutical Compositions

Disclosed herein, in certain embodiments, are pharmaceutical compositions comprising an amount of 2-hydroxypropyl-beta-cyclodextrin effective to treat CCE and/or one or more symptoms and/or clinical manifestations thereof, in a human; and an excipient. The excipient can be a pharmaceutically acceptable excipient.

The excipient may comprise a tonicity adjusting agent, a preservative, a solubilizing agent, a buffer, a solution (e.g., an IV solution), or any combination thereof. The tonicity adjusting agent can be dextrose, glycerol, sodium chloride, glycerin, mannitol, or a combination thereof. The preservative can be an antioxidant, an antimicrobial, a chelating agent, or a combination thereof. The antioxidant can be ascorbic acid, acetylcysteine, a sulfurous acid salt (e.g., bisulfite, metabisulfite), a monothioglycerol, or a combination thereof. The antimicrobial can be a phenol, meta-cresol, benzyl alcohol, paraben, benzalkonium chloride, chlorobutanol, thimerosal, phenylmercuric salts (e.g., acetate, borate, nitrate), or a combination thereof. The chelating agent can be calcium disodium ethylenediaminetetraacetic acid (EDTA), disodium EDTA, sodium EDTA, calcium versetamide sodium, calteridol, diethylenetriaminepenta acetic acid (DTPA), or a combination thereof. The solubilizing agent can be a surfactant or a co-solvent. The surfactant can be polyoxyethylene sorbitan monooleate (Tween 80), sorbitan monooleate polyoxyethylene sorbitan monolaurate (Tween 20), lecithin, polyoxyethylene-polyoxypropylene copolymers (Pluronics), or a combination thereof. The co-solvent can be propylene glycol, glycerin, ethanol, polyethylene glycol (PEG), sorbitol, dimethylacetamide, Cremophor EL, or a combination there. The polyethylene glycol can be PEG 300, PEG 400, PEG 600, PEG 3350, or PEG 4000. The buffer can comprise sodium acetate, acetic acid, glacial acetic acid, ammonium acetate, ammonium sulfate, ammonium hydroxide, arginine, aspartic acid, benzene sulfonic acid, benzoate sodium, benzoic acid, sodium bicarbonate, boric acid, sodium boric acid, sodium carbonate, citrate acid, sodium citrate, disodium citrate, trisodium citrate, diethanolamine, glucono delta lactone, glycine, glycine HCl, histidine, histidine HCl, hydrochloric acid, hydrobromic acid, lysine, maleic acid, meglumine, methanesulfonic acid, monoethanolamine, phosphate acid, monobasic potassium, dibasic potassium, monosodium phosphate, disodium phosphate, trisodium phosphate, sodium hydroxide, succinate sodium, sulfuric acid, tartarate sodium, tartaric acid, tromethamine (Tris), or a combination thereof.

The pharmaceutical composition can comprise at least about 4 g, at least about 10 g, at least about 50 g, at least about 100 g, at least about 150 g, at least about 200 g, or at least about 250 g of 2-hydroxypropyl-beta-cyclodextrin. In some embodiments, the pharmaceutical composition comprises at least about 4 g of 2-hydroxypropyl-beta-cyclodextrin. In some embodiments, the pharmaceutical composition comprises at least about 50 g of 2-hydroxypropyl-beta-cyclodextrin. In some embodiments, the pharmaceutical composition comprises at least about 100 g of 2-hydroxypropyl-beta-cyclodextrin. In some embodiments, the pharmaceutical composition comprises at least about 200 g of 2-hydroxypropyl-beta-cyclodextrin. In some embodiments, the pharmaceutical composition comprises from about 4 g to about 250 g of 2-hydroxypropyl-beta-cyclodextrin (e.g., from about 4 g to about 100 g, from about 4 g to about 50 g, from about 50 g to about 150 g, from about 50 g to about 250 g, from about 100 g to about 200 g, from about 100 g to about 250 g, from about 150 g to about 250 g).

The pharmaceutical composition may comprise an amount of 2-hydroxypropyl-beta-cyclodextrin effective to increase a circulating and/or systemic level of one or more oxysterol in a subject by at least about 10% (e.g., at 24 hours) after administering the pharmaceutical composition to the subject, such as by at least about 15%, at least about 20%, at least about 25%, at least about 30%, at least about 35%, at least about 40%, at least about 45%, at least about 50%, or greater.

The pharmaceutical composition may comprise an amount of 2-hydroxypropyl-beta-cyclodextrin effective to increase plasma cholesterol crystal dissolution capacity (CCDC) in the subject by at least about 10% (e.g., at 1 hour) after administering the pharmaceutical composition to a subject, such as by at least about 15%, at least about 20%, at least about 25%, at least about 30%, at least about 35%, at least about 40%, at least about 45%, at least about 50%, or greater.

The pharmaceutical composition may comprise an amount of 2-hydroxypropyl-beta-cyclodextrin effective to increase mRNA levels of one or more LXR transcription factor-regulated genes (e.g., ABCA1 and/or ABCG1) in a subject by at least about 10% (e.g., at 24 hours) after administering the pharmaceutical composition to the subject, such as by at least about 15%, at least about 20%, at least about 25%, at least about 30%, at least about 35%, at least about 40%, at least about 45%, at least about 50%, or greater.

The pharmaceutical composition can be formulated for single dose administration. The pharmaceutical composition can be formulated for intravenous administration. The pharmaceutical composition can be formulated to be isotonic.

Kits

Further provided herein are kits. In some cases, the kits include one or more container (e.g., a vial, a flask, a jar, a tube, an ampoule, etc.) containing one or more pharmaceutical compositions provided herein (e.g., 2-hydroxypropyl-beta-cyclodextrin and a pharmaceutically acceptable excipient). In some cases, the kit comprises more than one container (e.g., two, three, four, five, six, seven, eight, nine, ten, or more containers). In some cases, at least one of the one or more container is an IV infusion bag. The one or more container may include a single dosage of the pharmaceutical composition, or multiple dosages (e.g., two, three, four, five, six, seven, eight, nine, ten, or more) of the pharmaceutical composition. In some cases, the one or more container contains a concentrated amount of the pharmaceutical composition which is subsequently diluted, prior to administration, to achieve an effective dosage. The dosage may be any amount as described herein, effective to treat one or more indications described herein. The kit may further comprise one or more additional components for IV infusion of the pharmaceutical composition. In some cases, the kit comprises an IV infusion bag. In some cases, the kit comprises one or more solutions (e.g., saline) for mixing and/or diluting the pharmaceutical composition. In some cases, the kit comprises one or more of a catheter, a tubing, a syringe, and a needle. The kit may further comprise instructions, e.g., for administering the pharmaceutical composition to a subject for the use of treating any indication described herein (e.g., for reducing an amount of, reducing a size of, and/or changing the shape of circulating cholesterol crystals and/or clots comprising cholesterol crystals in an individual, and/or for treating cholesterol crystal embolization (CCE) and/or one or more symptoms thereof in an individual). The kit may be provided in a box, a bag, or any other suitable container.

In some aspects, the kit may comprise one or more additional active pharmaceutical ingredient (e.g., therapeutic compounds, drugs, etc.). In some cases, the kit may comprise a single container containing a pharmaceutical composition of the disclosure (e.g., 2-hydroxypropyl-beta-cyclodextrin and a pharmaceutically acceptable excipient) and the one or more additional active pharmaceutical ingredient. In other cases, the kit may comprise a first container containing a pharmaceutical composition of the disclosure (e.g., 2-hydroxypropyl-beta-cyclodextrin and a pharmaceutically acceptable excipient) and a second container containing the one or more additional active pharmaceutical ingredient.

EXAMPLES

Example 1. Plasma Obtained from a Subject Treated with 2-Hydroxypropyl-Beta-Cyclodextrin Demonstrates Cholesterol Crystal Dissolution Capacity A male human subject was treated with 2-hydroxypropyl-beta-cyclodextrin with single-ascending doses administered intravenously every 4 weeks according to Table 1 below.

TABLE 1

| Dose schedule | |
|---|---|
| Dose | Amount of 2-hydroxypropyl-beta-cyclodextrin |
| D0 (Week 0) | 500 mg/kg |
| M1 (Week 4) | 750 mg/kg |
| M2 (Week 8) | 1,000 mg/kg |
| M3 (Week 12) | 1,000 mg/kg |

For each dose, whole blood was collected pre-dose, post-dose (line flush), 1 hour post-dose, and 24 hours post-dose. Plasma was separated from the whole blood and subjected to a cholesterol crystal dissolution capacity (CCDC) assay using techniques similar to those described in the literature. The CCDC assay measures the ability of a sample to dissolve cholesterol crystals.

FIG. 1A depicts results of the CCDC assay. FIG. 1A demonstrates increased capability of blood plasma to dissolve cholesterol crystals after treatment with 2-hydroxypropyl-beta-cyclodextrin. This suggests that 2-hydroxpropyl-beta-cyclodextrin treatment increases plasma factors responsible for cholesterol crystal dissolution.

Figure 1B:
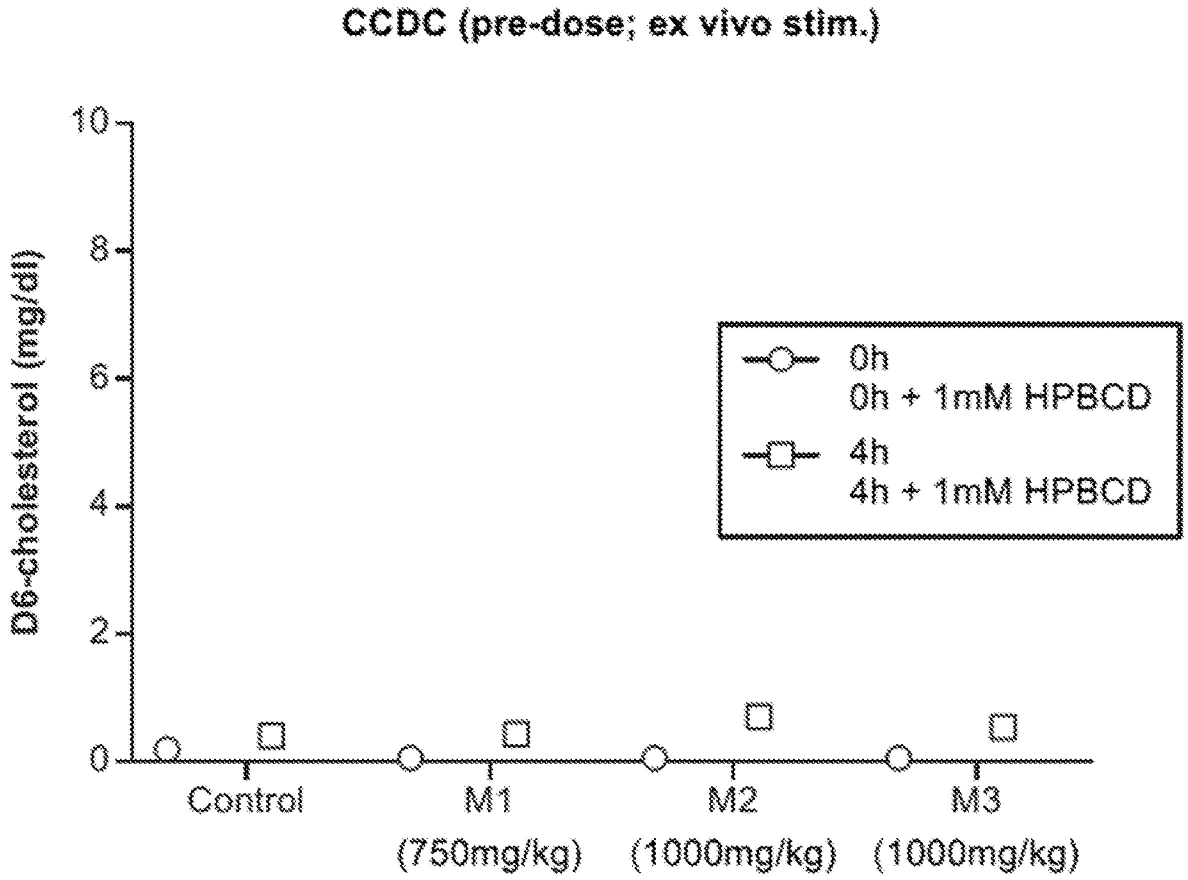

Blood plasma pre-dose was also incubated ex vivo with 2-hydroxypropyl-beta-cyclodextrin and the ability of the plasma to dissolve cholesterol crystals was measured. FIG. 1B demonstrates that plasma treated ex vivo with 2-hydroxypropyl-beta-cyclodextrin demonstrates increased capacity to dissolve cholesterol crystals.

Taken together, the data presented herein demonstrates that, in some embodiments, treatment of humans with 2-hydroxypropyl-beta-cyclodextrin increases plasma cholesterol crystal dissolution capacity which may lead to a reduction in the amount of and/or size of, and/or a change in the shape of circulating cholesterol crystals (and/or clots comprising cholesterol crystals). The data further demonstrates that, in some embodiments, treatment of humans with 2-hydroxypropyl-beta-cyclodextrin may be a suitable treatment for cholesterol crystal embolization, as described herein.

Figure 2A:
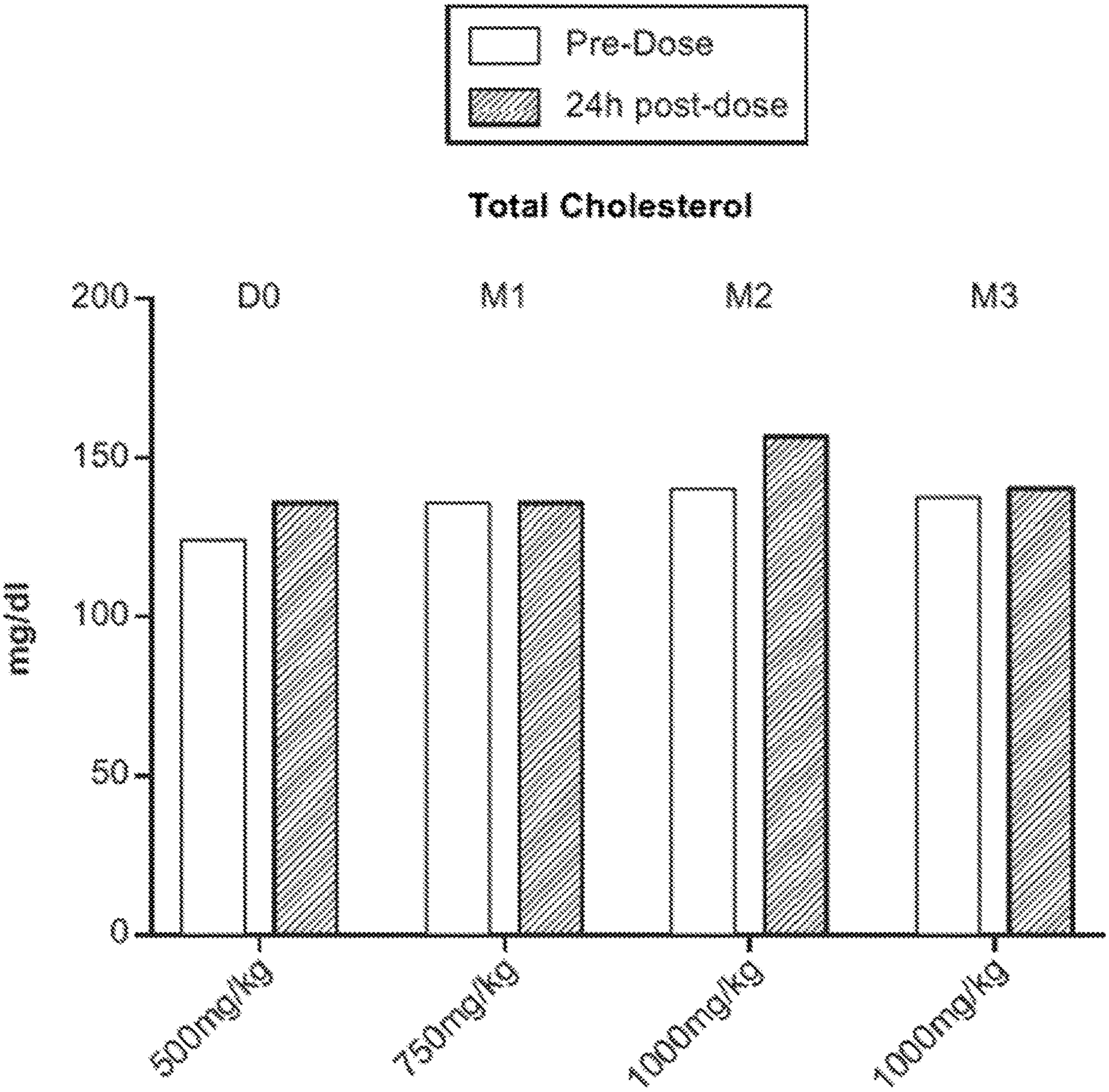
FIGS. 2A-2C depict a non-limiting example of total cholesterol levels and oxysterol levels in plasma obtained from a male human subject treated with increasing dosages of 2-hydroxypropyl-beta-cyclodextrin, in accordance with embodiments of the disclosure.
Figure 2B:
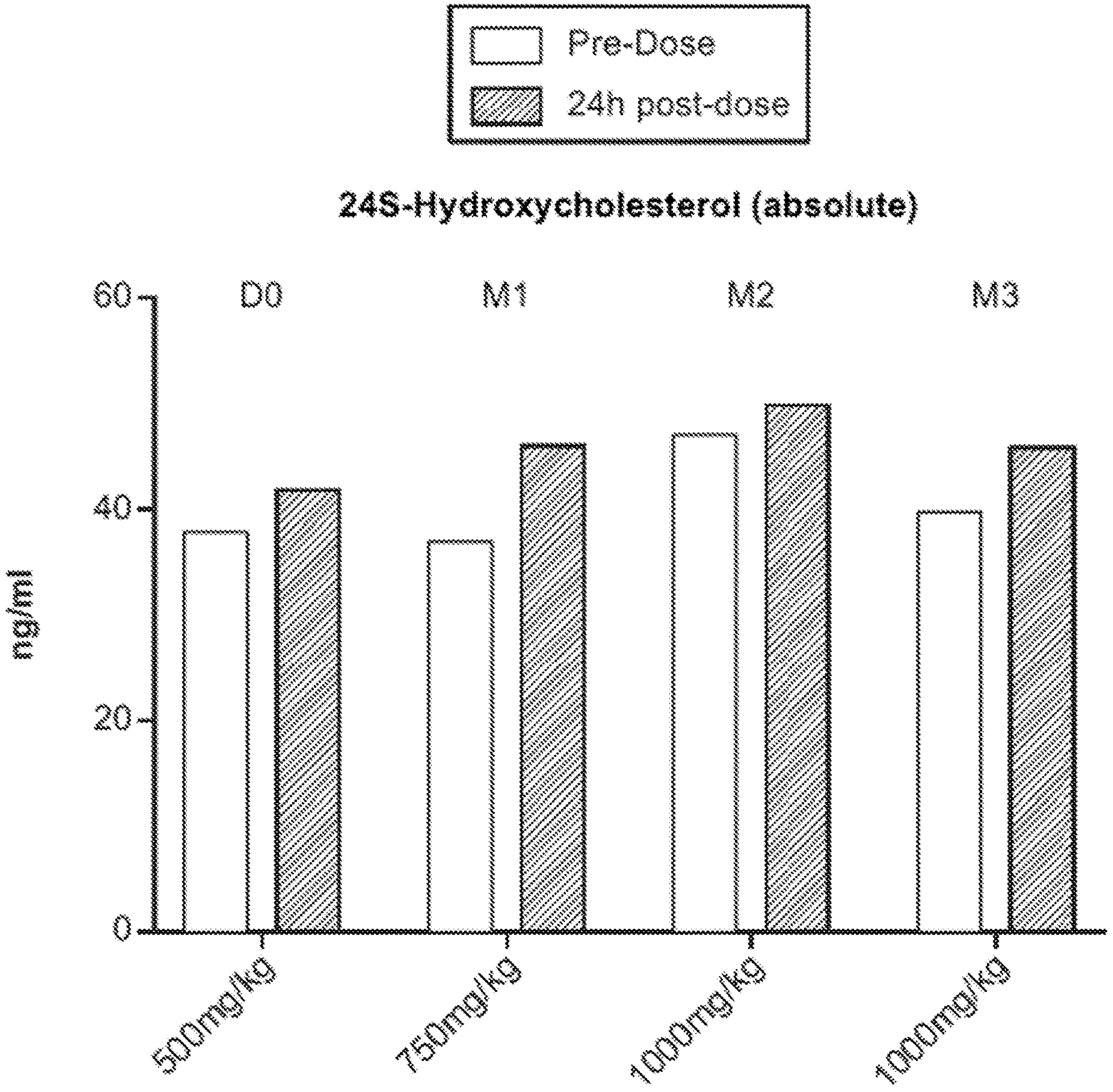
Figure 2C:
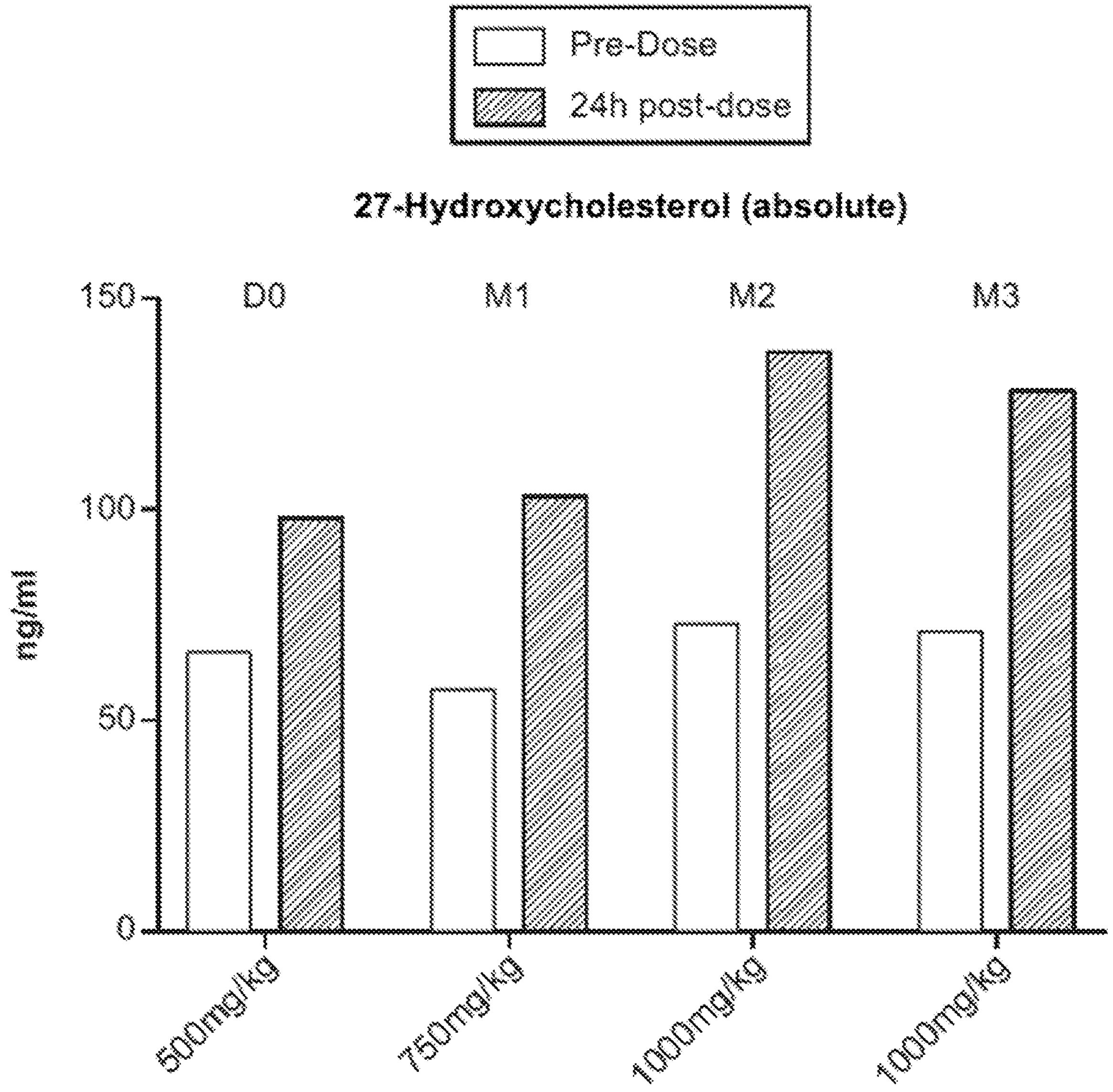
Figure 3A:
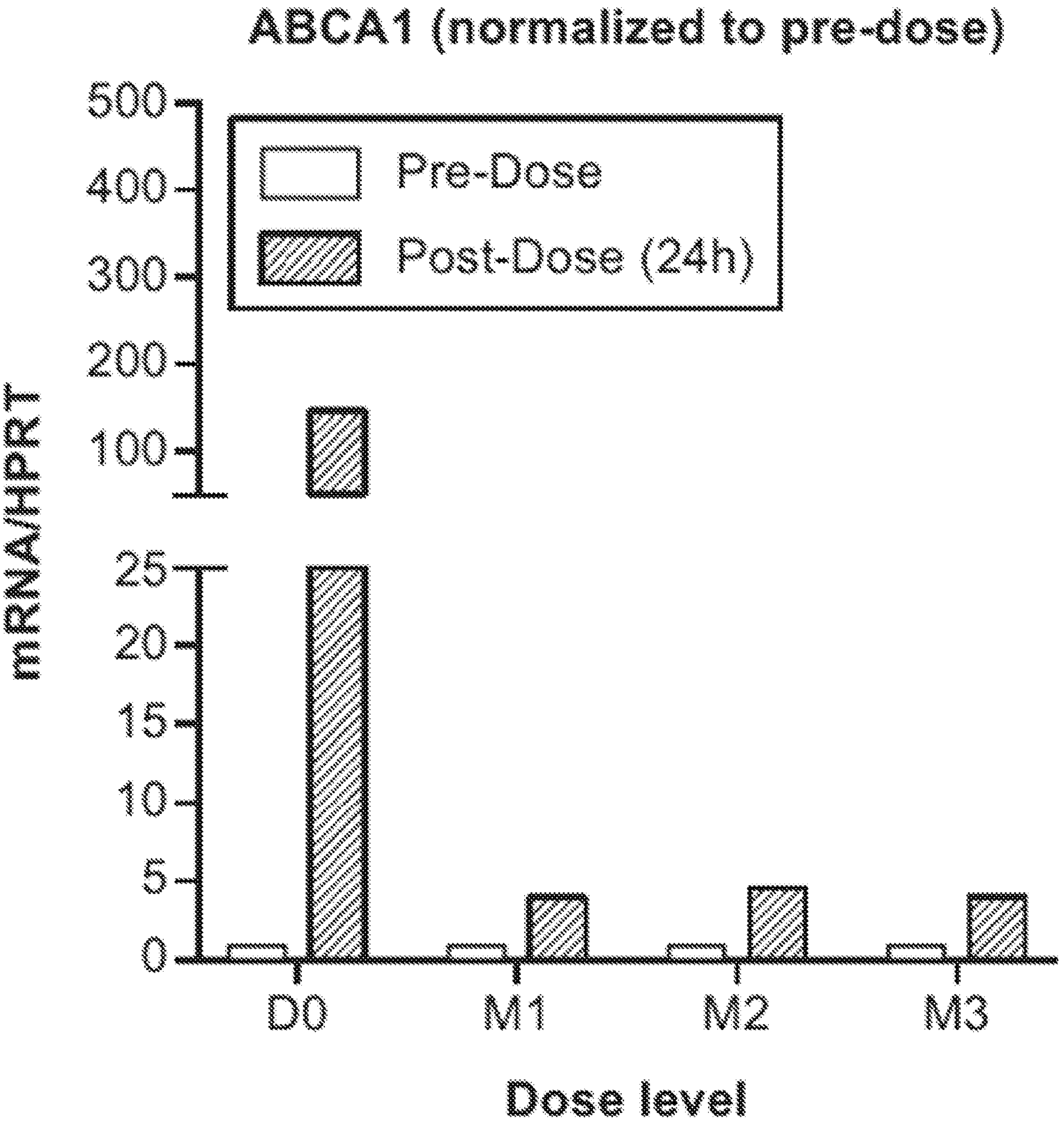
FIGS. 3A-3D depict a non-limiting example of mRNA levels of LXR transcription factor-regulated genes ABCA1 and ABCG1 in a male human subject treated with increasing dosages of 2-hydroxypropyl-beta-cyclodextrin, in accordance with embodiments of the disclosure.
Figure 3B:
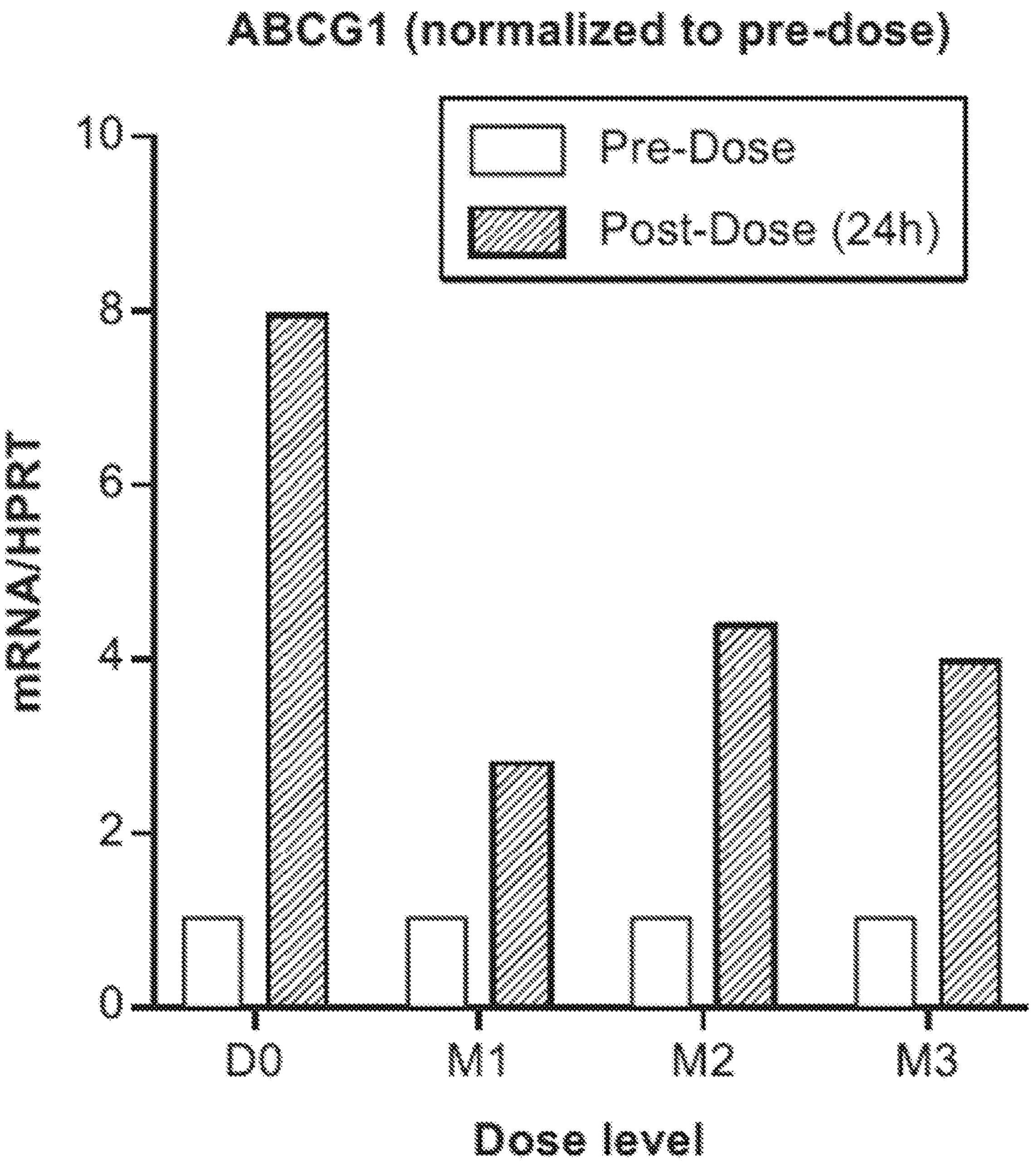
Figure 3C:
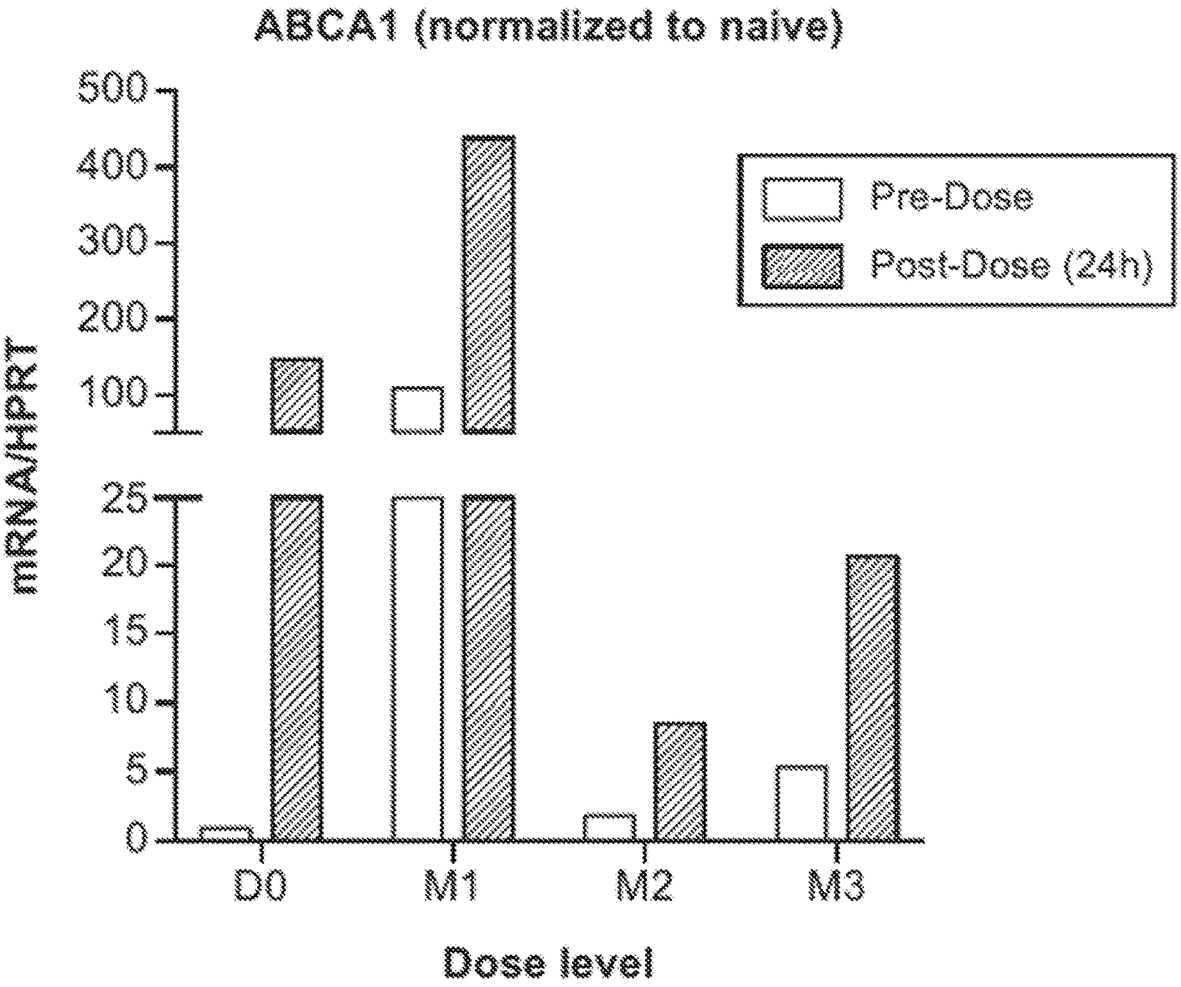
Figure 3D:
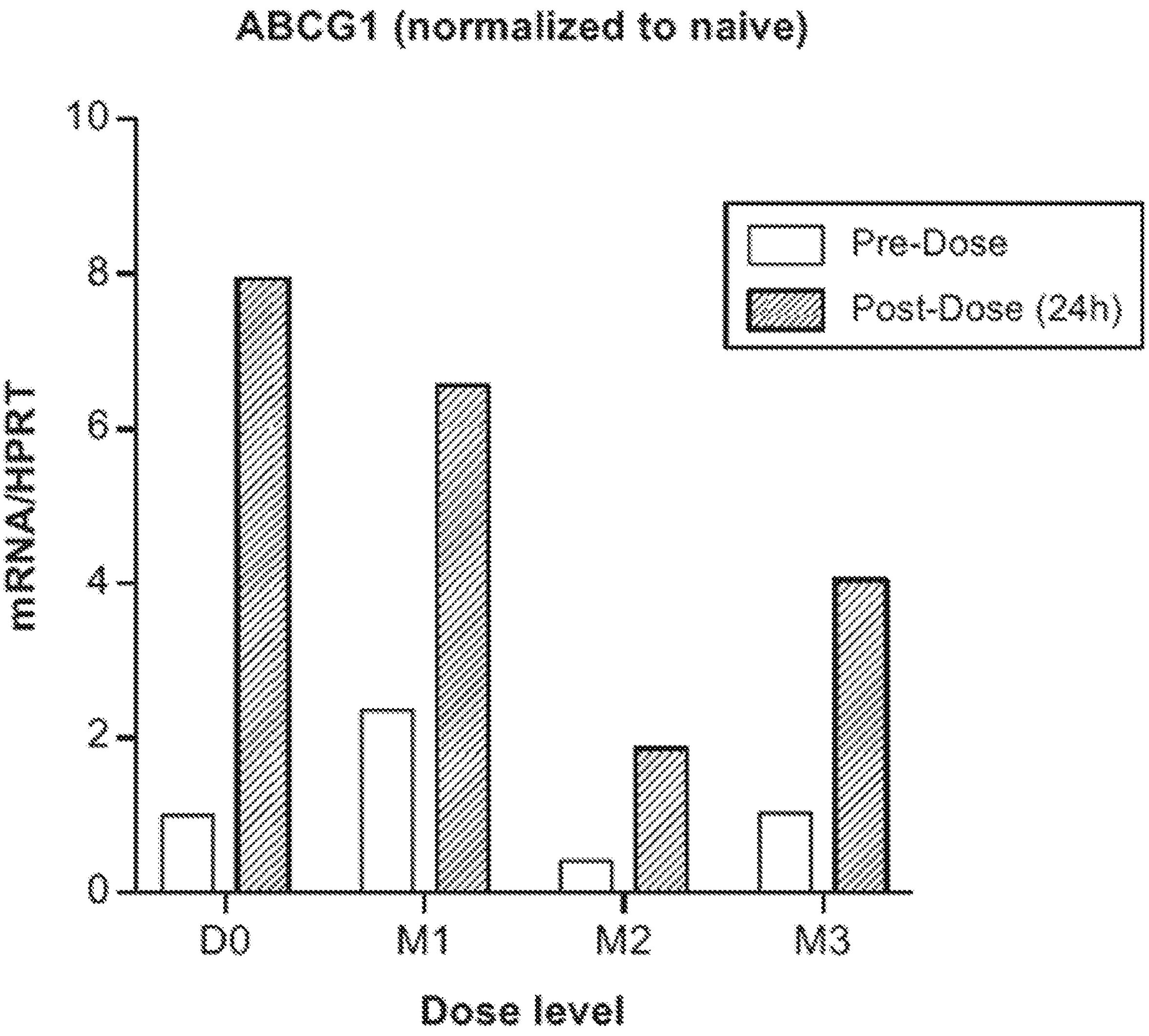

Example 2. Treatment with 2-Hydroxypropyl-Beta-Cyclodextrin Increases Sterol and Oxysterol Concentrations in a Human Subject In this Example, a male human subject was treated with 2-hydroxypropyl-beta-cyclodextrin according to Example 1, and plasma levels of 24S-hydroxycholesterol and 27-hydroxycholesterol were measured. FIGS. 2A-2C demonstrate that treatment with 2-hydroxypropyl-beta-cyclodextrin led to increased plasma levels of 24S-hydroxycholesterol and 27-hydroxycholesterol, whereas total cholesterol levels remained stable. 27-hydroxycholesterol is an endogenous LXR ligand leading to a downstream anti-inflammatory gene signature which may, in some embodiments, address the detrimental inflammatory response via NLRP3 inflammasome effects of cholesterol crystal embolization. The elevated 27-hydroxycholesterol is also a cellular marker of macrophage activation and increased activity for cholesterol crystal phagocytosis and clearance. Thus, the data demonstrates that, in some embodiments, treatment of humans with 2-hydroxypropyl-beta-cyclodextrin may lead to a reduction in the amount of and/or size of, and/or a change in the shape of circulating cholesterol crystals (and/or clots comprising cholesterol crystals). The data further demonstrates that, in some embodiments, treatment of humans with 2-hydroxypropyl-beta-cyclodextrin may be a suitable treatment for cholesterol crystal embolization, as described herein.

Example 3. Treatment with 2-Hydroxypropyl-Beta-Cyclodextrin Increases LXR Transcription Factor-Regulated Genes In this Example, a male human subject was treated with 2-hydroxypropyl-beta-cyclodextrin according to Example 1, and mRNA levels of the LXR transcription factor-regulated genes, ABCA1 and ABCG1, were measured. FIGS. 3A-3D demonstrate that treatment with 2-hydroxypropyl-beta-cyclodextrin led to increased mRNA levels of ABCA1 and ABCG1. This data demonstrates an increase in both ABCA1 and ABCG1 cholesterol transporters in peripheral blood. ABCA1 and ABCG1 are important cholesterol transporters and are responsible for cholesterol efflux from cells, loading of HDL particles for reverse cholesterol transport (RCT), and excretion via the hepatic pathway, to potentially reduce the cholesterol and cholesterol crystal emboli released into the vasculature and stabilize ruptured atherosclerotic plaque. Thus, the data demonstrates that, in some embodiments, treatment of humans with 2-hydroxypropyl-beta-cyclodextrin may lead to a reduction in the amount of and/or size of, and/or a change in the shape of circulating cholesterol crystals (and/or clots comprising cholesterol crystals). The data further demonstrates that, in some embodiments, treatment of humans with 2-hydroxypropyl-beta-cyclodextrin may be a suitable treatment for cholesterol crystal embolization, as described herein.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of reducing an amount of, reducing a size of, and/or changing the shape of circulating cholesterol crystals and/or clots comprising cholesterol crystals in a human individual, the method comprising: administering a therapeutically effective amount of 2-hydroxypropyl-beta-cyclodextrin to the individual, thereby reducing the amount of, reducing the size of, and/or changing the shape of circulating cholesterol crystals and/or clots comprising cholesterol crystals in the individual, wherein the therapeutically effective amount is from about 500 mg/kg to about 1000 mg/kg.

2. The method of claim 1, wherein the size of circulating cholesterol crystals and/or clots comprising cholesterol crystals is reduced by at least about 10%, relative to the size of circulating cholesterol crystals and/or clots comprising cholesterol crystals prior to the administering with the 2-hydroxypropyl-beta-cyclodextrin.

3. The method of claim 1, wherein the amount of circulating cholesterol crystals and/or clots comprising cholesterol crystals is reduced by at least about 10%, relative to the amount of circulating cholesterol crystals and/or clots comprising cholesterol crystals prior to the administering with the 2-hydroxypropyl-beta-cyclodextrin.

4. The method of claim 1, wherein the treating reduces an incidence or severity of cholesterol crystal embolization (CCE) in the individual.

5. The method of claim 1, wherein the individual is at least 30 years old.

6. The method of claim 1, wherein the administering further comprises: (i) administering, at a first time point, a therapeutically effective first dose of 2-hydroxypropyl-beta-cyclodextrin to the individual; and (ii) administering, at a second time point, a therapeutically effective second dose of 2-hydroxypropyl-beta-cyclodextrin to the individual.

7. The method of claim 6, wherein the second time point is at least 4 hours after the first time point.

8. The method of claim 1, further comprising subjecting the individual to a vascular or cardiovascular trauma after the administration.

9. The method of claim 1, wherein the administration improves renal function, a reduces dermatologic manifestation, reduces eosinophilia, reduces a hematologic abnormality, reduces a complement level, reduces proteinuria, in the individual.

10. The method of claim 1, wherein the therapeutically effective amount is from about 750 mg/kg to about 1000 mg/kg.

11. The method of claim 1, wherein the therapeutically effective amount is a first dose of about 500 mg/kg of 2-hydroxypropyl-beta-cyclodextrin and a second dose of about 750 mg/kg to about 1000 mg/kg of 2-hydroxypropyl-beta-cyclodextrin at least about 1 week after the first dose.

12. The method of claim 1, wherein the administration is intravenous.

* * * * *